US012766118B2

(12) United States Patent
Millet et al.

(10) Patent No.: US 12,766,118 B2
(45) **Date of Patent: *Oct. 20, 2026**

(54) ENRICHED R-BETA-HYDROXYBUTYRATE COMPOSITION

(71) Applicant: AXCESS GLOBAL SCIENCES, LLC, Washington, UT (US)

(72) Inventors: Gary Millet, Salt Lake City, UT (US); Ryan Lowery, Tampa, FL (US); Jacob Wilson, Tampa, FL (US); Terry Lacore, Melissa, TX (US)

(73) Assignee: AXCESS GLOBAL SCIENCES, LLC, Washington, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/637,946

(22) Filed: Apr. 2, 2026

(65) Prior Publication Data

US 2026/0232609 A1 Aug. 13, 2026

Related U.S. Application Data

(60) Continuation of application No. 19/303,084, filed on Aug. 18, 2025, which is a continuation-in-part of application No. 18/911,045, filed on Oct. 9, 2024, now Pat. No. 12,496,283, which is a continuation-in-part of application No. 18/591,994, filed on Feb. 29, 2024, now Pat. No. 12,128,020, which is a continuation of application No. 18/219,556, filed on Jul. 7, 2023, now Pat. No. 12,251,362, application No. 19/637,946 is a continuation-in-part of application No. 18/105,030, filed on Feb. 2, 2023, said application No. 18/219,556 is a continuation of application No. 17/367,206, filed on Jul. 2, 2021, now Pat. No. 12,109,182, said application No. 18/105,030 is a division of application No. 17/210,646, filed on Mar. 24, 2021, now Pat. No. 11,806,324, which is a continuation-in-part of application No. 16/783,844, filed on Feb. 6, 2020, now Pat. No. 11,103,470, which is a continuation-in-part of application No. 16/409,501, filed on May 10, 2019, now Pat. No. 10,596,131, which is a continuation-in-part of application No. 16/272,165, filed on Feb. 11, 2019, now Pat. No. 10,596,129, which is a continuation-in-part of application No. 16/224,408, filed on Dec. 18, 2018, now Pat. No. 10,588,876, which is a division of application No. 15/936,820, filed on Mar. 27, 2018, now Pat. No. 10,245,242, said application No. 17/367,206 is a continuation-in-part of application No. 15/491,924, filed on Apr. 19, 2017, now Pat. No. 11,173,138.

(60) Provisional application No. 62/590,063, filed on Nov. 22, 2017, provisional application No. 62/324,798, filed on Apr. 19, 2016.

(51) Int. Cl.

| | |
|---|---|
| ***A61K 31/19*** | (2006.01) |
| ***A61K 9/00*** | (2006.01) |
| ***A61K 31/522*** | (2006.01) |
| ***A61P 3/04*** | (2006.01) |
| ***A61P 25/28*** | (2006.01) |

(52) U.S. Cl.

CPC ............ *A61K 31/19* (2013.01); *A61K 9/0053* (2013.01); *A61K 31/522* (2013.01); *A61P 3/04* (2018.01); *A61P 25/28* (2018.01)

(58) Field of Classification Search

CPC .... A61K 31/19; A61K 9/0053; A61K 31/522; A61P 25/28; A61P 3/04

See application file for complete search history.

(56) References Cited

U.S. PATENT DOCUMENTS

| | | | |
|---|---|---|---|
| 9,138,420 | B2 | 9/2015 | D'Agostino et al. |
| 10,245,242 | B1 | 4/2019 | Millet |
| 10,588,876 | B2 | 3/2020 | Millet |
| 10,596,129 | B2 | 3/2020 | Millet |
| 10,596,131 | B2 | 3/2020 | Millet |
| 10,973,786 | B2 | 4/2021 | Millet |
| 11,103,470 | B2 | 8/2021 | Millet |
| 11,690,817 | B2 | 7/2023 | Millet |
| 2018/0021274 | A1 | 1/2018 | Arnold |
| 2019/0376098 | A1 | 12/2019 | Liao et al. |

FOREIGN PATENT DOCUMENTS

| | | |
|---|---|---|
| CN | 110035991 A | 7/2019 |

*Primary Examiner* — Shirley V Gembeh

(74) *Attorney, Agent, or Firm* — Workman Nydegger

(57) ABSTRACT

Beta-hydroxybutyrate compositions for administering ketone bodies to a subject include a non-racemic mixture of R-beta-hydroxybutyrate and S-beta-hydroxybutyrate enriched with R-beta-hydroxybutyrate so as to contain more than 50% and less than 100% by enantiomeric equivalents of R-beta-hydroxybutyrate and less than 50% and more than 0% by enantiomeric equivalents of S-beta-hydroxybutyrate. Non-racemic mixtures of beta-hydroxybutyrate include one or more R-beta-hydroxybutyrate salts, one or more S-beta-hydroxybutyrate salts, one or more R-beta-hydroxybutyrate esters, one or more S-beta-hydroxybutyrate esters, R-beta-hydroxybutyric acid, S-beta-hydroxybutyric acid, and combinations thereof.

20 Claims, 12 Drawing Sheets

| Subject | Condition | Baseline | 30 minutes | 60 minutes | 90 minutes | 120 minutes | 180 minutes |
|---|---|---|---|---|---|---|---|
| A | 10g DL-BHB | 0.2 | 0.7 | 0.5 | 0.3 | 0.2 | 0.2 |
| B | 10g DL-BHB | 0.1 | 0.9 | 0.6 | 0.3 | 0.2 | 0.2 |
| C | 10g DL-BHB | 0.1 | 0.5 | 0.2 | 0.1 | 0.1 | 0.1 |
| D | 10g DL-BHB | 0.2 | 0.8 | 0.6 | 0.3 | 0.2 | 0.1 |
| Average | | 0.15 | 0.725 | 0.475 | 0.25 | 0.175 | 0.15 |
| | | | | | | | |
| A | 10g R-BHB | 0.2 | 1.8 | 0.7 | 0.4 | 0.3 | 0.2 |
| B | 10g R-BHB | 0.2 | 1.5 | 0.7 | 0.3 | 0.2 | 0.2 |
| C | 10g R-BHB | 0.1 | 0.7 | 0.3 | 0.2 | 0.2 | 0.1 |
| D | 10g R-BHB | 0.1 | 1.5 | 1.2 | 0.6 | 0.2 | 0.2 |
| Average | | 0.15 | 1.375 | 0.725 | 0.375 | 0.225 | 0.175 |
| | | | | | | | |
| A | 5g R-BHB | 0.3 | 0.6 | 0.3 | 0.4 | 0.3 | 0.4 |
| B | 5g R-BHB | 0.1 | 0.8 | 0.7 | 0.2 | 0.2 | 0.2 |
| C | 5g R-BHB | 0.1 | 0.4 | 0.2 | 0.2 | 0.2 | 0.1 |
| D | 5g R-BHB | 0.1 | 0.7 | 0.3 | 0.2 | 0.1 | 0.1 |
| Average | | 0.15 | 0.625 | 0.375 | 0.25 | 0.2 | 0.2 |

*FIG. 1*

Total Fat Mass Results

| Scan Date | Age | Fat Mass (g) | Change/Month vs Baseline | Change/Month vs Previous | Change vs Baseline | Change vs Previous |
|---|---|---|---|---|---|---|
| 12/17/2016 | 51 | 32748 | -1545 | -1545 | -5177 | -5177 |
| 09/05/2016 | 51 | 37925 | | | | |

ENRICHED R-BETA-HYDROXYBUTYRATE COMPOSITION

CROSS-REFERENCE TO RELATED APPLICATIONS

This application is a continuation of U.S. patent application Ser. No. 19/303,084, filed Aug. 18, 2025, which is a continuation-in-part of U.S. patent application Ser. No. 18/911,045, filed Oct. 9, 2024, now U.S. Pat. No. 12,496,283, which is a continuation-in-part of U.S. patent application Ser. No. 18/591,994, filed Feb. 29, 2024, now U.S. Pat. No. 12,128,020, which is a continuation of U.S. patent application Ser. No. 18/219,556, filed Jul. 7, 2023, now U.S. Pat. No. 12,251,362, which is a continuation of U.S. patent application Ser. No. 17/367,206, filed Jul. 2, 2021, now U.S. Pat. No. 12,109,182, which is a continuation-in-part of U.S. patent application Ser. No. 15/491,924, filed Apr. 19, 2017, now U.S. Pat. No. 11,173,138, which claims the benefit of U.S. Provisional Application No. 62/324,798, filed Apr. 19, 2016.

This Application is also a continuation-in-part of U.S. patent application Ser. No. 18/105,030, filed Feb. 2, 2023, which is a division of U.S. patent application Ser. No. 17/210,646, filed Mar. 24, 2021, now U.S. Pat. No. 11,806,324, which is a continuation-in-part of U.S. patent application Ser. No. 16/783,844, filed Feb. 6, 2020, now issued U.S. Pat. No. 11,103,470, which is a continuation-in-part of U.S. patent application Ser. No. 16/409,501, filed May 10, 2019, now issued U.S. Pat. No. 10,596,131, which is a continuation-in-part of U.S. patent application Ser. No. 16/272,165, filed Feb. 11, 2019, now issued U.S. Pat. No. 10,596,129, which is a continuation-in-part of U.S. patent application Ser. No. 16/224,408, filed Dec. 18, 2018, now issued U.S. Pat. No. 10,588,876, which is a division of U.S. patent application Ser. No. 15/936,820, filed Mar. 27, 2018, now U.S. Pat. No. 10,245,242, which claims the benefit of U.S. Provisional Patent Application No. 62/590,063, filed Nov. 22, 2017.

The foregoing patents and patent applications are incorporated herein by reference in their entirety.

TECHNICAL FIELD

The present invention relates to administration of butyrate, beta-hydroxybutyrate, and related compounds.

BACKGROUND

Currently, beta-hydroxybutyrate salts can be administered orally or intravenously in humans to promote weight loss and/or ketosis. However, the excess intake of salts such as sodium, magnesium, and potassium may be unwarranted (e.g., high blood pressure, stroke, damage to organs, gastrointestinal problems, etc.). Thus, many people may not be able to tolerate administration of beta-hydroxybutyrate salts in amounts to promote or sustain weight loss and/or ketosis. Polymers of beta-hydroxybutyrate have also been administered to humans to promote ketosis. However, since polymers must be processed by the body to deliver beta-hydroxybutyrate to the individual, the delivery is slow and/or a larger amount of the polymer must be administered to deliver a specified amount of beta-hydroxybutyrate.

SUMMARY

In various implementations, a pharmaceutically effective amount of butyrate, beta-hydroxybutyrate, related compounds, and/or one or more other compounds may be administered to an individual. For example, the pharmaceutically effective amount of the beta-hydroxybutyrate, related compounds, and/or one or more other compounds may be administered to cause weight loss, assist weight maintenance, elevate blood ketone levels, maintain blood ketone levels, reduce blood glucose levels, maintain blood glucose levels, improve focus, improve energy, improve cognitive function, treat traumatic brain injury, treat diabetes, treat neurological disorders, treat cancer, treat inflammatory conditions, suppress appetite, provide anti-aging effects, anti-glycation, treat epilepsy, treat depression, improve performance, improve strength, improve muscle mass, promote fat loss, improve body composition, and/or for use as a medicament, etc. The pharmaceutically effective amount of butyrate, beta-hydroxybutyrate, related compounds, and/or combinations thereof may be administered to healthy individuals and/or not healthy individuals (e.g., with diseases and/or disorders).

Implementations may include one or more of the following features. The beta-hydroxybutyrate may include a racemic mixture of beta-hydroxybutyrate, individual isomers of beta-hydroxybutyrate, namely R-beta-hydroxybutyrate (also known as D-beta-hydroxybutyrate) and S-beta-hydroxybutyrate (also known as L-beta-hydroxybutyrate), or a non-racemic mixture enriched with R-beta-hydroxybutyrate relative to S-beta-hydroxybutyrate. Beta-hydroxybutyrate compositions may include one or more beta-hydroxybutyrate salts, one or more beta-hydroxybutyrate esters, beta-hydroxybutyric acid, and combinations thereof. The beta-hydroxybutyrate may include related compounds, such as ketone body precursors (e.g., 1,3-butanediol and medium chain fatty acids). The beta-hydroxybutyrate may be coupled to a compound such as an amino acid. The beta-hydroxybutyrate may include beta-hydroxybutyrate salt and beta-hydroxybutyrate esters, in some implementations. Other compounds may include short chain fatty acids, short chain triglycerides, medium chain fatty acids, medium chain triglycerides, long chain fatty acids, long chain triglycerides, berberine, berberine metabolites, dihydroberberine, tetrahydroberberine and/or combinations thereof. One or more of the other compounds may be unencapsulated and/or encapsulated.

In various implementations, a composition may be administered to induce and/or maintain ketosis. The composition may include approximately 0.5 g to approximately 10 g of R-beta-hydroxybutyrate.

Implementations may include one or more of the following features. The amount of the composition administered may include approximately 0.5 to approximately 3 g of R-beta-hydroxybutyrate. The composition may include additional composition, such as compositions that are capable of independently increasing ketone levels, inducing ketosis, and/or maintaining ketosis. In some implementations, the composition may include additional compositions to provide other health benefits (e.g., increase mental acuity, strength, etc.). For example, the composition may include fatty acids and/or esters of fatty acids. For example, the composition may include a short chain fatty acid, an ester of short chain fatty acid, a medium chain fatty acid, an ester of medium chain fatty acid, a long chain fatty acid, or an ester of long chain fatty acid. The composition may include flavoring(s), vitamin(s), mineral(s), and/or binder(s). The composition may be administered up to 5 times daily. The administration of the composition may increase strength, mental acuity, metabolism, fat loss, fat oxidation, motor function, muscle mass, and/or combinations thereof. In some implementations, the 0.5 to 10 g of R-beta-hydroxybutyrate administered includes R-beta-hydroxybutyrate and at least one of a polymer of R-beta-hydroxybutyrate or R-beta-hydroxybutyrate-complex.

Administration of the composition may induce and/or maintains ketosis in an individual. Ketogenic compositions described herein may be administered to a subject in therapeutically effective dosages and/or in frequencies to induce or sustain ketosis. In some embodiments, a single dose will include an amount of non-racemic mixture of R-beta-hydroxybutyrate and S-beta-hydroxybutyrate ranging from about 0.5 gram to about 25 grams, or about 0.75 gram to about 20 grams, or about 1 gram to about 15 grams, or about 1.5 grams to about 12 grams.

Implementations may include one or more of the following features. The R-beta-hydroxybutyrate may include R-beta-hydroxybutyrate salt, R-beta-hydroxybutyrate-amino acid complex, and/or R-beta-hydroxybutyrate polymer. The additional compounds may include fatty acids and/or esters of fatty acids. The fatty acids and/or esters may include natural (e.g., cream, coconut oil, macadamia oil, etc.) and/or artificial fatty acids and/or esters of fatty acids. For example, the composition may include a short chain fatty acid, an ester of short chain fatty acid, a medium chain fatty acid, an ester of medium chain fatty acid, a long chain fatty acid, or an ester of long chain fatty acid. In some implementations, additional compound(s) may include polymer(s) of beta-hydroxybutyrate, D,L-beta-hydroxybutyrate, butyrate, butyric acid, and/or triglyceride tributyrin. The additional compound(s) may include berberine, dihydroberberine, and/or tetrahydroberberine.

In various implementations, pharmaceutically effective amounts of R-beta-hydroxybutyrate and amino acid may be administered for inducing and/or maintaining ketosis.

Implementations may include one or more of the following features. The amount of R-beta-hydroxybutyrate to induce and/or maintain ketosis in an individual may be less than or equal to half of the amount of D,L-beta-hydroxybutyrate to induce and/or maintain the same level of ketosis (e.g., as measured by blood ketone levels). In some implementations, the amount of R-beta-hydroxybutyrate to induce and/or maintain ketosis in an individual may be less than the amount of D,L-beta-hydroxybutyrate or L-beta-hydroxybutyrate to induce and/or maintain the same level of ketosis. The composition may include approximately 1 g to approximately 5 grams of R-beta-hydroxybutyrate and approximately 0.5 to 2 g of amino acid. The amino acid may include Leucine. The composition may include a mixture and/or complex of the R-beta-hydroxybutyrate and amino acid. At least a portion of the R-beta-hydroxybutyrate may be complexed with the amino acid, in some implementations. For example, a portion of the R-beta-hydroxybutyrate may be administered in the composition as a salt and/or polymer and another portion of the R-beta-hydroxybutyrate may be administered as a complex with an amino acid (e.g., leucine). In some implementations, the composition may include at least one R-beta-hydroxybutyrate salt (e.g., in additional to the pharmaceutically effective amounts of R-beta-hydroxybutyrate in the composition and/or as the pharmaceutically effective amounts of R-beta-hydroxybutyrate).

In various implementations, a composition for maintaining or increasing weight loss may include approximately 0.5 g to approximately 15 g of R-beta-hydroxybutyrate, one or more flavorings, one or more vitamins, one or more minerals, one or more binders, and/or one or more liquid carriers. The R-beta-hydroxybutyrate comprises one or more salts of R-beta-hydroxybutyrate salt. The composition may be orally administered to maintaining and/or increasing weight loss in an individual.

Implementations may include one or more of the following features. The liquid carrier may include water. The amount of R-beta-hydroxybutyrate salt may include approximately 0.5 to approximately 5 g of R-beta-hydroxybutyrate salt. The composition may include at least one polymer of beta-hydroxybutyrate and at least one salt of R-beta-hydroxybutyrate. The administration of the composition increases mental acuity. The administration of the composition increases at least one of metabolism, fat loss, fat oxidation, motor function, and/or muscle mass. The composition may be administered up to 5 times daily. The R-beta-hydroxybutyrate salt in the composition may include sodium R-beta-hydroxybutyrate, potassium R-beta-hydroxybutyrate, magnesium R-beta-hydroxybutyrate, and/or calcium R-beta-hydroxybutyrate salt.

In various implementations, a composition for maintaining or inducing ketosis may include approximately 0.5 g to approximately 15 g of R-beta-hydroxybutyrate, one or more flavorings, one or more vitamins, one or more minerals, one or more binders, and/or one or more liquid carriers. The R-beta-hydroxybutyrate comprises one or more salts of R-beta-hydroxybutyrate salt. The composition may be orally administered to maintain and/or induce ketosis in an individual.

Implementations may include one or more of the following features. The amount of R-beta-hydroxybutyrate salt in the composition may include approximately 0.5 to approximately 5 g of R-beta-hydroxybutyrate salt. The one or more salts of R-beta-hydroxybutyrate may include sodium R-beta-hydroxybutyrate, potassium R-beta-hydroxybutyrate, calcium R-beta-hydroxybutyrate, and/or magnesium R-beta-hydroxybutyrate. The liquid carrier may include water, milk, and/or coconut water. The administration of the composition may increase metabolism, fat loss, fat oxidation, motor function, and/or muscle mass. The administration of the compound may increase mental acuity, cognitive functioning, mood, energy, alertness, focus, and/or performance.

In various implementations, a composition for maintaining or inducing ketosis may include approximately 0.5 g to approximately 15 g of R-beta-hydroxybutyrate, an additional compound capable of increasing ketone levels independently, one or more flavorings, one or more vitamins, one or more minerals, one or more binders, and/or one or more liquid carriers. The R-beta-hydroxybutyrate comprises one or more salts of R-beta-hydroxybutyrate salt. The additional compound may include less than approximately 500 mg of caffeine. The composition may be orally administered to maintain and/or induce ketosis in an individual.

Implementations may include one or more of the following features. The composition may include approximately 5 mg to approximately 50 mg of caffeine. The composition comprises include approximately 0.5 g to approximately 5 g of R-beta-hydroxybutyrate and approximately 5 mg to approximately 50 mg of caffeine. The one or more salts of R-beta-hydroxybutyrate may include sodium R-beta-hydroxybutyrate, potassium R-beta-hydroxybutyrate, calcium R-beta-hydroxybutyrate, and/or magnesium R-beta-hydroxybutyrate. The administration of the composition may increase at least one of weight loss, metabolism, fat loss, fat oxidation, motor function, muscle mass, mental acuity, cognitive functioning, mood, energy, alertness, focus, and/or performance. The liquid carrier may include water, milk, and/or coconut water.

In some embodiments, the composition is in the form of a solid form of beta-hydroxybutyric acid, which can be mixed with water or aqueous beverage to form an aqueous beta-hydroxybutyric acid solution. Dilute, ready to drink aqueous beta-hydroxybutyric acid solutions can have a concentration of beta-hydroxybutyric acid in a range of about 0.4% w/v to about 6% w/v. In some embodiments, solid beta-hydroxybutyric acid compositions can be provided for later mixing with water or aqueous beverage by the user, such as with water, juice, drink, energy shot, or other aqueous composition to a concentration in a range of about 0.4% w/v to about 6% w/v. Alternatively, solid beta-hydroxybutyric acid compositions can be mixed with water to form a concentrated solution that comprises beta-hydroxybutyric acid in a range of about 6% w/v to about 60% w/v, and then diluted by the user as desired, such as from about 2 to about 30 times, with water, juice, drink, or other aqueous composition, as desired.

In some embodiments, the solid beta-hydroxybutyric acid compositions may be contain or be mixed with one or more nutritionally or pharmaceutically acceptable carriers or additives in addition to water. For example, beta-hydroxybutyric acid compositions may optionally include at least one additive selected from acetoacetic acid, 1,3-butanediol, beta-hydroxybutyrate esters, acetoacetate esters, vitamins, minerals, central nervous system stimulants, nootropics, edible acids, amino acids, muscle-promoting compounds (e.g., beta-hydroxy beta-methylbutyrate), one or more cannabinoids (e.g., tetrahydrocannabinol and/or cannabidiol), and the like.

In various embodiments, solid beta-hydroxybutyric acid compositions may include enantiomerically pure R-beta-hydroxybutyric acid, enantiomerically pure S-beta-hydroxybutyric acid, a racemic mixture of R- and S-beta-hydroxybutyric acid (i.e., a mixture having a 1:1 enantiomeric ratio of R-beta-hydroxybutyric acid and S-beta-hydroxybutyric acid), a non-racemic mixture enriched with the R-enantiomer, or a non-racemic mixture enriched with the S-enantiomer. In some embodiments it is advantageous to include at least some amount of S-beta-hydroxybutyric acid in addition to or instead of R-beta-hydroxybutyric acid. Beta-hydroxybutyric acid enriched with, or that contains enantiomerically pure, S-beta-hydroxybutyric acid may be administered in higher doses than compositions enriched with, or that contain enantiomerically pure, R-beta-hydroxybutyric acid to obtain the same rapid supply of R-beta-hydroxybutyrate in the body.

Beta-hydroxybutyric acid compositions disclosed herein may function to induce and/or sustain ketosis in a subject to which the composition is administered without significantly affecting electrolyte balance. This removes an otherwise limiting factor as to how much beta-hydroxybutyrate can be administered when administered in salt form. In addition, beta-hydroxybutyrate esters, particularly by themselves or when the primary source of beta-hydroxybutyrate, have an unpleasant taste and are not always well tolerated.

In some embodiments, beta-hydroxybutyric acid compositions can be provided as a powder or other solid that can be added to water, drink or food to form an ingestible aqueous solution, gel or suspension. Alternatively, beta-hydroxybutyric acid compositions can be provided as an aqueous solution, such as in the form of a beverage, a concentrated energy shot, or mouth spray for fast delivery and absorption. Beta-hydroxybutyric acid compositions can be provided as gel, such as an energy gel. Beta-hydroxybutyric acid compositions can be provided as a food product, such as a sauce or condiment.

Beta-hydroxybutyric acid compositions can be useful as a weight loss supplement, as treatment for high blood glucose or type II diabetes, as brain tonic, as athletic performance enhancer, as preventative against metabolic dysfunction, mitochondrial defect, insulin resistance, as adjunct to a ketogenic diet, as anti-aging supplement, and for other uses associated with improved metabolic health. Beta-hydroxybutyric acid compositions can be used in a method for increasing ketone body level in a subject in need thereof, including promoting and/or sustaining ketosis in the subject, comprising administering to the subject a nutritionally or pharmaceutically effective amount of beta-hydroxybutyric acid. Benefits of increased ketone body level in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizure, improved mood, increased strength, increased muscle mass, or improved body composition.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which:

FIG. 1 illustrates a table of blood ketone levels over time for 4 subjects for an implementation of an example administration of D,L-beta-hydroxybutyrate and R/D-beta-hydroxybutyrate.

Like reference symbols in the various drawings indicate like elements.

DETAILED DESCRIPTION

Figure 2:
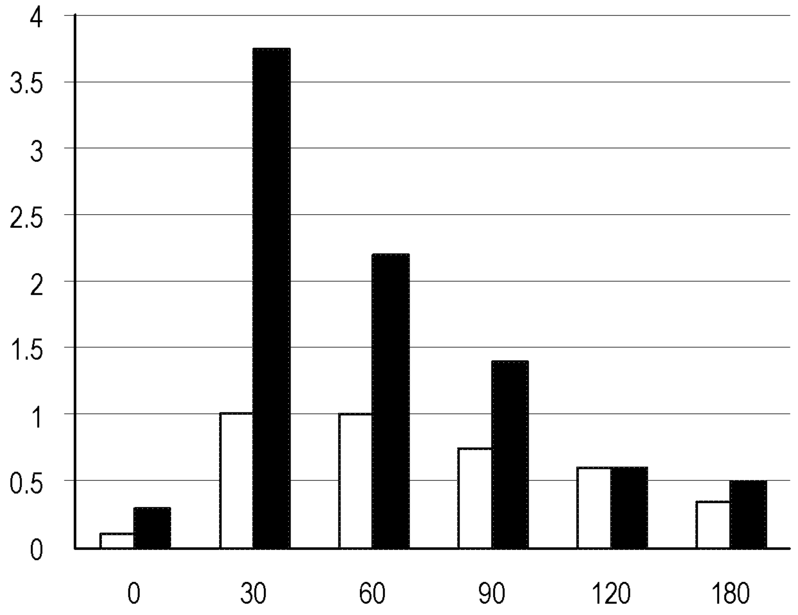
FIG. 2 illustrates a table of blood ketone levels over time for an implementation of an example administration of the microencapsulated butyrate compared to traditional sodium butyrate.

In various implementations, compounds such as butyrate, beta-hydroxybutyrate and/or related compounds (e.g., derivatives, esters, polymers, etc.) can be administered alone or in combination with one or more other compounds. Beta-hydroxybutyric acid compositions can be provided in solid or powder form and used to form aqueous solutions, beverages, gels, and food products. Administration of a pharmaceutically effective amount of these compound(s) may promote and/or maintain weight loss and/or ketosis. In some implementations, blood ketone levels and/or blood glucose levels may be reduced and/or maintained within a predetermined range when a pharmaceutically effective amount of one or more compounds are administered. In some implementations, a health of an individual (e.g., strength, symptoms of disease, mental acuity, fasting glucose levels, etc.) may be improved and/or maintained by administration of a compound that includes butyrate, beta-hydroxybutyrate and/or related compounds (e.g., derivatives, esters, polymers, etc.).

In various implementations butyrate, beta-hydroxybutyrate and/or related compounds may be administered to a human. Beta-hydroxybutyrate (e.g., R-beta-hydroxybutyrate, L-beta-hydroxybutyrate, and/or D,L-beta-hydroxybutyrate) may include beta-hydroxybutyrate salts and/or beta-hydroxybutyrate esters. In some implementations, beta-hydroxybutyrate may include beta-hydroxybutyrate bound to another compound (e.g., amino acids) and/or polymers of beta-hydroxybutyrate. For example, beta-hydroxybutyrate (e.g., R-beta-hydroxybutyrate, L-beta-hydroxybutyrate, and/or D,L-beta-hydroxybutyrate) may include beta-hydroxybutyrate salts, beta-hydroxybutyrate esters, beta-hydroxybutyrate sodium salt (e.g., sodium beta-hydroxybutyrate), beta-hydroxybutyrate potassium salt (e.g., potassium beta-hydroxybutyrate), beta-hydroxybutyrate calcium salt (e.g., calcium beta-hydroxybutyrate), beta-hydroxybutyrate magnesium salt (e.g., magnesium beta-hydroxybutyrate), beta-hydroxybutyrate lithium salt (e.g., lithium beta-hydroxybutyrate), sodium beta-hydroxybutyrate, arginine beta-hydroxybutyrate, lysine beta-hydroxybutyrate, histidine beta-hydroxybutyrate, ornithine beta-hydroxybutyrate, creatine beta-hydroxybutyrate, agmatine beta-hydroxybutyrate, or citrulline beta-hydroxybutyrate, other appropriate organic salts that include beta-hydroxybutyrate, and/or combinations thereof. In some implementations, the beta-hydroxybutyrate may include beta-hydroxybutyrate salts including (calcium, sodium, magnesium, potassium, zinc, selenium, chromium, other appropriate minerals, and/or combinations thereof. In some implementations, the beta-hydroxybutyrate may be complexed and/or coupled to another compound (e.g., amino acid and/or berberine) and a beta-hydroxybutyrate salt may include a complex (e.g., chelate) that includes a mineral (e.g., calcium, zinc, etc.) and the beta-hydroxybutyrate compound coupled to another compound. The beta-hydroxybutyrate may include single isomer beta-hydroxybutyrate and/or polymer beta-hydroxybutyrate. For example, R-beta-hydroxybutyrate may include single isomer R-beta-hydroxybutyrate and/or polymer R-beta-hydroxybutyrate. In some implementations, beta-hydroxybutyrate may be administered with 1,3-butanediol, ethyl acetoacetate, ethyl beta-hydroxybutyrate.

The beta-hydroxybutyrate may include racemic mixtures and/or individual isomers of beta-hydroxybutyrate. In some implementations, one or more specific chiralities of beta-hydroxybutyrate may be utilized. For example, R-beta-hydroxybutyrate (also referred to as D-beta-hydroxybutyrate), S-beta-hydroxybutyrate (also referred to as L-beta-hydroxybutyrate), and/or mixtures (e.g., racemic and non-racemic mixtures) thereof may be utilized. In some implementations, R-beta-hydroxybutyrate may be included in the composition (e.g., a more purified form of R-beta-hydroxybutyrate rather than D,L-beta-hydroxybutyrate). For example, R-beta-hydroxybutyrate may include less than approximately 10 percent, less than approximately 5 percent, or less than approximately 1 percent L-beta-hydroxybutyrate. R-beta-hydroxybutyrate may have a greater bioavailability than other chiralities of beta-hydroxybutyrate. R-beta-hydroxybutyrate may have a greater impact on a health of an individual (e.g., due to decreased side effects; increase ketone levels, weight loss, mental acuity, fat loss, etc.) than L-beta-hydroxybutyrate and/or D,L-beta-hydroxybutyrate. In some implementations, R-beta-hydroxybutyrate may cause improvements in health not capable by L-beta-hydroxybutyrate and/or D,L-beta-hydroxybutyrate. R-beta-hydroxybutyrate may have less impurities due to manufacturing, such as less crotonic acid (e.g., which can be harmful to individuals), than other forms of beta-hydroxybutyrate (e.g., L-beta-hydroxybutyrate and/or D,L-beta-hydroxybutyrate). In some implementations, R-beta-hydroxybutyrate may be more capable of binding with other compounds (e.g., purine, lysine, potassium, and/or other amino acids; dihydroberberine; etc.) to deliver the beta-hydroxybutyrate to a human. Thus, R-beta-hydroxybutyrate (e.g., greater than 90 percent purity of R-beta-hydroxybutyrate and less than 10 percent L-beta-hydroxybutyrate, or greater than 95 percent purity of R-beta-hydroxybutyrate and less than 5 percent L-beta-hydroxybutyrate) and/or mixtures with R-beta-hydroxybutyrate may be administered to humans. In some implementations, unexpectedly, a smaller amount of R-beta-hydroxybutyrate may be as pharmaceutically effective (e.g., in increasing and/or maintaining weight loss; in increasing and/or maintaining elevated ketone levels, etc.) or more pharmaceutically effective as D,L-beta-hydroxybutyrate (e.g., racemic mixture of D- and L-beta-hydroxybutyrate). For example, approximately half an amount of R-beta-hydroxybutyrate may be administered to achieve the approximately the same efficacy as D,L-beta-hydroxybutyrate and/or L-beta-hydroxybutyrate. The R-beta-hydroxybutyrate may be more bioavailable than other chiralities of beta-hydroxy butyrate and thus allow a smaller effective amount than other chiralities. Thus, by utilizing R-beta-hydroxybutyrate, the administration amount of beta-hydroxybutyrate to be reduced (e.g., when compared to the administration amount of D,L-beta-hydroxybutyrate) while providing a pharmaceutically effective amount, such as (e.g., for weight loss and/or maintenance; for elevating and/or maintaining blood ketone levels). Reducing the amount of beta-hydroxybutyrate, when the beta-hydroxy butyrate is provided in salt form, may reduce a user's intake of the cation of the salt (e.g., sodium, potassium, etc.). Since intake of some of these cations in beta-hydroxybutyrate salts, such as sodium, potassium, magnesium, and calcium, in amounts greater than a predetermined recommended amount may cause health problems (e.g., organ damage, gastrointestinal problems, etc.), reducing the amount of beta-hydroxybutyrate salt by using R-beta-hydroxybutyrate may inhibit side effects and/or health problems associated salts combined with beta-hydroxybutyrate administration in users.

In some embodiments, a non-racemic mixture of R-beta-hydroxybutyrate and S-beta-hydroxybutyrate is enriched with R-beta-hydroxybutyrate so as to contain more than 50% and less than 100% by enantiomeric equivalents of R-beta-hydroxybutyrate and less than 50% and more than 0% by enantiomeric equivalents of S-beta-hydroxybutyrate. For example, non-racemic mixtures of R-beta-hydroxybutyrate and S-beta-hydroxybutyrate may contain 50.5% to 99.5%, 51% to 99%, 52% to 98%, 53% to 97%, 55% to 95%, 55% to 89%, 57% to 87%, or 60% to 80% by enantiomeric equivalents of the R-beta-hydroxybutyrate enantiomer and 49.5% to 0.5%, 49% to 1%, 48% to 2%, 47% to 3%, 45% to 5%, 45% to 11%, 43% to 13%, 41% to 15%, or 40% to 20% by enantiomeric equivalents of the S-beta-hydroxybutyrate enantiomer.

In some implementations, a pharmaceutically effective amount of R-beta-hydroxybutyrate may be administered in an individual to promote and/or maintain ketosis, cause weight loss and/or manage weight, and/or increase blood ketone levels. For example, approximately 0.1 g to approximately 50 g of R-beta-hydroxybutyrate may be administered to an individual. In some implementations, approximately 0.1 g to approximately 15 g of R-beta-hydroxybutyrate may be administered to an individual. In some implementations, approximately 1 g to approximately 10 g of beta-hydroxybutyrate may be administered, for example, once a day to 5 times a day (e.g., to administer up to 50 g of beta-hydroxybutyrate). The administration may cause weight loss and/or maintenance; elevated beta-hydroxybutyrate levels in the blood; elevated, reduced, and/or maintenance of blood ketone levels; induction and/or maintenance of ketosis; and/or reduction; improve mental acuity; improve focus; improve energy; improve cognitive function; reduce traumatic brain injury; improve diabetes; improve glucose tolerance; decrease blood glucose levels; reduce neurological disorders and/or symptoms thereof; improve cancer and/or symptoms thereof, improve inflammatory conditions; suppressing appetite; improve symptoms associated with aging; provide anti-glycation affects; improve epilepsy and/or symptoms thereof; improve depression and/or symptoms thereof; improve performance; improve strength; increase muscle mass; increase fat loss; improve body composition; improve energy; improve focus; improve cognitive function; improve mood and/or well-being; and/or combinations thereof. The beta-hydroxybutyrate (e.g., R-beta-hydroxybutyrate) may be administered in healthy and not healthy individuals (e.g., individuals with diseases and/or disorders).

In some embodiments, the composition is in the form of a solid form of beta-hydroxybutyric acid, which can be mixed with water or aqueous beverage to form an aqueous beta-hydroxybutyric acid solution. In some embodiments, the composition is in the form of an aqueous beta-hydroxybutyric acid solution. Dilute, ready to drink aqueous beta-hydroxybutyric acid solutions formed by mixing solid beta-hydroxybutyric acid with water or other aqueous drink, liquid or beverage can have a concentration that is sufficiently diluted such that volumes of about 4 oz. (about 120 ml) to about 16 oz. (about 475 ml) can deliver a quantity of ketone bodies in a range of about 0.5 gram to about 25 grams, without harming the stomach or causing significant acidosis. For example, dilute aqueous beta-hydroxybutyric acid solutions can have a concentration of beta-hydroxybutyric acid in a range of about 0.4% w/v to about 6% w/v, or about 0.6% w/v to about 5.5% w/v, or about 0.9% w/v to about 5% w/v, or about 1.2% w/v to about 4.5% w/v, or about 1.5% w/v to about 4% w/v.

In some embodiments, solid beta-hydroxybutyric acid compositions can be provided for later mixing with water or aqueous beverage by the user, such as with water, juice, drink, energy shot, or other aqueous composition to a concentration in a range of about 0.4% w/v to about 6% w/v, or about 0.6% w/v to about 5.5% w/v, or about 0.9% w/v to about 5% w/v, or about 1.2% w/v to about 4.5% w/v, or about 1.5% w/v to about 4% w/v. Alternatively, solid beta-hydroxybutyric acid compositions can be mixed with water to form a concentrated solution that comprises beta-hydroxybutyric acid in a range of about 6% w/v to about 60% w/v, or about 8% w/v to about 55% w/v, or about 10% w/v to about 50% w/v, or about 12.5% w/v to about 45% w/v, or about 15% w/v to about 40% w/v, and then diluted by the user as desired, such as from about 2 to about 30 times, or about 3 to about 25 times, or about 4 to about 2 times, or about 5 to about 15 times, with water, juice, drink, or other aqueous composition, as desired.

In some embodiments, beta-hydroxybutyric acid compositions can be free or substantially free of beta-hydroxybutyrate salts so as to contain less than 4%, less than 3%, or less than 2.5%, or less than 2%, or less than 1.5%, or less than 1% of one or more beta-hydroxybutyrate salts by combined weight of beta-hydroxybutyric acid and beta-hydroxybutyrate salt(s). Including 0.5-4%, or 0.8-3%, or 1-2.5%, of one or more beta-hydroxybutyrate salts (96-99.5%, or 97-99.2%, or 97.5-99% of beta-hydroxybutyric acid) has been found to substantially prevent self-polymerization of solid beta-hydroxybutyric acid.

In some embodiments, the beta-hydroxybutyric acid compositions may contain one or more nutritionally or pharmaceutically acceptable carriers or additives in in the solid form and/or water or other aqueous beverage to which it is added. For example, beta-hydroxybutyric acid compositions may optionally include at least one additive selected from acetoacetic acid, 1,3-butanediol, beta-hydroxybutyrate esters, acetoacetate salts, acetoacetate esters, vitamins, minerals, central nervous system stimulants, nootropics, edible acids, amino acids, muscle-promoting compounds (e.g., beta-hydroxy beta-methylbutyrate), one or more cannabinoids (e.g., tetrahydrocannabinol and/or cannabidiol), and the like.

In various embodiments, beta-hydroxybutyric acid compositions may include enantiomerically pure R-beta-hydroxybutyric acid, enantiomerically pure S-beta-hydroxybutyric acid, a racemic mixture of R- and S-beta-hydroxybutyric acid (i.e., a mixture having a 1:1 enantiomeric ratio of R-beta-hydroxybutyric acid and S-beta-hydroxybutyric acid), a non-racemic mixture enriched with the R-enantiomer, or a non-racemic mixture enriched with the S-enantiomer. In some embodiments it is advantageous to include at least some amount of S-beta-hydroxybutyric acid in addition to or instead of R-beta-hydroxybutyric acid.

In embodiment, beta-hydroxybutyric acid compositions contain a non-racemic mixture enriched with the R-enantiomer, such as greater than 50% and less than 100% by enantiomeric equivalents of exogenous R-beta-hydroxybutyric acid and less than 50% and greater than 0% by enantiomeric equivalents of exogenous S-beta-hydroxybutyric acid. In some embodiments, a non-racemic mixture of R- and S-beta-hydroxybutyric acid forms contain 50.5% to 99.5%, 51% to 99%, 52% to 98%, 53% to 97%, 55% to 95%, 55% to 89%, 57% to 87%, or 60% to 80% by enantiomeric equivalents of R-beta-hydroxybutyric acid and 49.5% to 0.5%, 49% to 1%, 48% to 2%, 47% to 3%, 45% to 5%, 45% to 11%, 43% to 13%, 41% to 15%, or 40% to 20% by enantiomeric equivalents of S-beta-hydroxybutyric acid.

In a second embodiment, beta-hydroxybutyric acid compositions contain a non-racemic mixture enriched with the S-enantiomer, such as greater than 50% and less than 100% by enantiomeric equivalents of exogenous S-beta-hydroxybutyric acid and less than 50% and greater than 0% by enantiomeric equivalents of exogenous R-beta-hydroxybutyric acid. In some embodiments, a non-racemic mixture of S- and R-beta-hydroxybutyric acid forms contain 50.5% to 99.5%, 51% to 99%, 52% to 98%, 53% to 97%, 55% to 96%, 57% to 93%, 60% to 90%, or 65% to 85% by enantiomeric equivalents of S-beta-hydroxybutyric acid and 49.5% to 0.5%, 49% to 1%, 48% to 2%, 47% to 3%, 45% to 4%, 43% to 7%, 40% to 10%, or 35% to 15% by enantiomeric equivalents of R-beta-hydroxybutyric acid.

In a third embodiment, beta-hydroxybutyric acid compositions contain a racemic (or near racemic) mixture of R-beta-hydroxybutyric acid and S-beta-hydroxybutyric acid, i.e., that contains 50% by enantiomeric equivalents of exogenous R-beta-hydroxybutyric acid and 50% by enantiomeric equivalents of exogenous S-beta-hydroxybutyric acid. A near racemic mixture that is not a perfect 50:50 mixture of R- and S-enantiomers may include about 49.9% to about 50.1%, or about 49.92% to about 50.08%, or about 49.94% to about 50.06%, or about 49.96% to about 50.04%, or about 49.98% to about 50.02%, by enantiomeric equivalents of R-beta-hydroxybutyrate and about 50.1% to about 49.9%, or about 50.06% to about 49.94%, or about 50.04% to about 49.96%, or about 50.02% to about 49.98%, by enantiomeric equivalents of S-beta-hydroxybutyrate.

In a fourth embodiment, beta-hydroxybutyric acid compositions contain enantiomerically pure S-beta-hydroxybutyric acid, i.e., that contains 100% by enantiomeric equivalents of exogenous S-beta-hydroxybutyric acid and 0% by enantiomeric equivalents of R-beta-hydroxybutyric acid.

In a fifth embodiment, beta-hydroxybutyric acid compositions contain enantiomerically pure R-beta-hydroxybutyric acid, i.e., that contains 100% by enantiomeric equivalents of exogenous R-beta-hydroxybutyric acid and 0% by enantiomeric equivalents of S-beta-hydroxybutyric acid. Because exogenous R-beta-hydroxybutyric acid dissolved in water to form an aqueous solution with a "water buffer" is not found in nature, it is not a "natural product".

Beta-hydroxybutyric acid enriched with, or that contains enantiomerically pure, S-beta-hydroxybutyric acid may be administered in higher doses than compositions enriched with, or that contain enantiomerically pure, R-beta-hydroxybutyric acid to obtain the same rapid supply of R-beta-hydroxybutyrate in the body. In such cases, it may be desirable to include incrementally higher, but still small, amounts of beta-hydroxybutyrate salts, such as less than 4.0%, or less than 3.75%, or less than 3.5%, or less than 3.25%, or less than 3.0%, or less than 2.75%, or less than 2.5% or less than 2.25%, or less than 2%, or less than 1.75%, or less than 1.5%, or less than 1.25%, of such salts by combined weight of beta-hydroxybutyric acid and beta-hydroxybutyrate salt(s), in order to further offset the greater acidity of higher concentrations and/or amounts of beta-hydroxybutyric acid in compositions that are enriched with, or contain enantiomerically pure, S-beta-hydroxybutyric acid.

In some embodiments, beta-hydroxybutyric acid compositions can be provided as a powder or other solid form, which can be mixed with water or an aqueous solution, to form a beverage, a concentrated energy shot, or mouth spray for fast delivery and absorption. Beta-hydroxybutyric acid compositions can be formed into or provided as gel, such as an energy gel. Beta-hydroxybutyric acid compositions can be formed into or provided as a food product, such as a sauce or condiment. Beta-hydroxybutyric acid compositions can be provided as a powder or other solid that can be added to water, drink or food to form an ingestible aqueous solution, gel or suspension.

Beta-hydroxybutyric acid compositions disclosed herein may function to induce and/or sustain ketosis in a subject to which the composition is administered without significantly affecting electrolyte balance. This removes an otherwise limiting factor as to how much beta-hydroxybutyrate can be administered when administered in salt form. In addition, beta-hydroxybutyrate esters, particularly by themselves or when the primary source of beta-hydroxybutyrate, have an unpleasant taste and are not always well tolerated.

Beta-hydroxybutyric acid compositions can be useful as a weight loss supplement, as treatment for high blood glucose or type II diabetes, as brain tonic, as athletic performance enhancer, as preventative against metabolic dysfunction, mitochondrial defect, insulin resistance, as adjunct to a ketogenic diet, as anti-aging supplement, and for other uses associated with improved metabolic health.

Beta-hydroxybutyric acid compositions can be used in a method for increasing ketone body level in a subject in need thereof, including promoting and/or sustaining ketosis in the subject, comprising administering to the subject a nutritionally or pharmaceutically effective amount of beta-hydroxybutyric acid. Benefits of increased ketone body level in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, anti-glycation, reduction in epileptic seizure, improved mood, increased strength, increased muscle mass, or improved body composition.

Beta-hydroxybutyrate is the deprotonated form of beta-hydroxybutyric acid having the formula $CH_3CH_2OHCH_2COOH$. The deprotonated form present at typical biological pH levels is $CH_3CH_2OHCH_2COO$—. The general chemical structure of beta-hydroxybutyrate is:

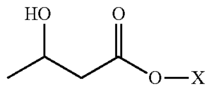

where, X can be hydrogen, metal ion, amino cation such as from an amino acid, alkyl, alkenyl, aryl, or acyl.

When X is a hydrogen, the compound is beta-hydroxybutyric acid. When X is a metal ion or an amino cation, the compounds is a beta-hydroxybutyrate salt. When X is alkyl, alkenyl, aryl, or acyl, the compounds is a beta-hydroxybutyrate ester. The foregoing compounds can be in any desired physical form, such as crystalline, powder, solid, liquid, solution, suspension, or gel.

Unless otherwise specified, the term "salt" does not mean or imply any particular physical state, such as a crystalline, powder, other solid form, dissolved in water to form a liquid solution, dispersed in a liquid to form a suspension, or gel. A salt can be formed in solution, such as by at least partially neutralizing beta-hydroxybutyric acid with a strong or weak base, such as an alkali or alkaline earth metal hydroxide, carbonate, or bicarbonate, basic amino acid, and the like.

In some embodiments, the composition is in the form of a beta-hydroxybutyrate mixed salt-acid composition that includes one or more beta-hydroxybutyrate salts and beta-hydroxybutyric acid. In some embodiments, the mixed salt-acid composition contains less than 100% of one or more beta-hydroxybutyrate salts and greater than 0% free beta-hydroxybutyric acid, such as up to 99.9%, 99.8%, 99.7%, 99.6%, 99.5%, 99.4%, 99.3%, 99.2%, 99.1%, 99%, 98.8%, 98.65%, 98.5%, 98.35%, 98.2%, 98%, 97.75%, 97.5%, 97.25%, or 97%, and at least 75%, 80%, 85%, 90%, 92%, 94%, 95%, 96%, or 97%, by molar equivalents of one or more R-beta-hydroxybutyrate and/or S-beta-hydroxybutyrate salts, and at least 0.1%, 0.2%, 0.3%, 0.4%, 0.5%, 0.6%, 0.7%, 0.8%, 0.9%, 1%, 1.2%, 1.35%, 1.5%, 1.65%, 1.8%, 2%, 2.25%, 2.5%, 2.75%, or 3%, and less than 25%, 20%, 15%, 10%, 8%, 6%, 5%, 4%, or 3%, by molar equivalents of free R-beta-hydroxybutyric acid and/or free S-beta-hydroxybutyric acid.

In some implementations, the beta-hydroxybutyrate, such as R-beta-hydroxybutyrate, may be administered with and/or coupled to a compound such as an amino acid. For example, beta-hydroxybutyrate may be coupled to (e.g., chemically bonded to) amino acids, such as leucine, lysine, arginine, histidine, ornithine, creatine, agmatine, citrulline and/or combinations thereof. In some implementations, R-beta-hydroxybutyrate may be utilized rather than other chiralities since R-beta-hydroxybutyrate may be more easily bound to leucine, purine, lysine, and/or other amino acids. Administration of beta-hydroxy butyrate that is coupled to an amino acid may reduce the intake of cations associated with beta-hydroxybutyrate salts (e.g., which may inhibit side effects associated with administration) and/or allow administration of another compound that has health benefits (e.g., administration of some amino acid may promote smooth muscle growth and/or cell repair). In some implementations, approximately 0.5 g to approximately 10 g of amino acid may be administered with a beta-hydroxybutyrate. For example, less than approximately 50 g of R-beta-hydroxybutyrate and less than approximately 60 mg of an amino acid, such as leucine, may be administered daily. In some implementations, approximately 0.5 g to approximately 2 g of an amino acid, such as leucine, may be administered with a beta-hydroxybutyrate. For example, approximately the composition administered may include approximately 0.1 g to approximately 7 g of R-beta-hydroxybutyrate and approximately 1-3 g of leucine. The R-beta-hydroxybutyrate and the leucine may be a mixture, administered separately and proximate in timing, a complex, and/or administered in any other appropriate manner.

In some implementations, the composition may include R-beta-hydroxybutyrate salt and beta-hydroxybutyrate-amino acid complex (e.g., beta-hydroxybutyrate bound to amino acid, such as R-beta-hydroxybutyrate-leucine complex). For example, an individual may be administered a first weight amount of sodium beta-hydroxybutyrate and a second weight amount of beta-hydroxybutyrate amino-acid complex. The first amount and the second amount may be different or the same.

In some implementations, the beta-hydroxybutyrate composition may include beta-hydroxybutyrate salt and beta-hydroxybutyrate esters. For example, an individual may be administered a first weight amount of sodium beta-hydroxybutyrate and a second weight amount of beta-hydroxybutyrate ester. The first amount and the second amount may be different or the same. The beta-hydroxybutyrate salt and the beta-hydroxybutyrate ester may be a bound complex, a mixture of compounds, and/or separately administered approximately concurrently. In some implementations, the beta-hydroxybutyrate ester may be in powdered form (e.g., plated beta-hydroxybutyrate ester), liquid and/or gel form. The combination of beta-hydroxybutyrate salt and beta-hydroxybutyrate ester during administration may allow less salt to be utilized while producing a result (e.g., weight maintenance and/or loss; enhanced and/or maintained ketosis; elevated blood ketone levels; blood glucose reduction and/or maintenance; increase in energy; increase in mood; increase in performance; and/or increase in cognitive function). In some implementations, elevated ketone levels (e.g., elevated blood ketone levels) may increase energy, mood, performance, and/or cognitive function in users. For example, the administration of the first amount of beta-hydroxybutyrate salt may cause a first level of blood ketone level, which may be maintained by processing of the second amount of the beta-hydroxybutyrate ester (e.g., as the body of the individual processes the beta-hydroxy butyrate ester the level of beta-hydroxy butyrate in the blood, and thus blood ketone level, may also increase over time to enhance and/or maintain the initial elevation caused by of the administered beta-hydroxybutyrate salt.). For example, a ratio of beta-hydroxy butyrate to beta-hydroxybutyrate ester may be approximately 1 beta-hydroxybutyrate salt: approximately 1 beta-hydroxybutyrate ester to approximately 1 beta-hydroxybutyrate salt: approximately 20 beta-hydroxybutyrate ester. The ratio of beta-hydroxybutyrate to beta-hydroxybutyrate ester may be approximately 20 beta-hydroxybutyrate salt: approximately 1 beta-hydroxybutyrate ester to approximately 1 beta-hydroxybutyrate salt: approximately 20 beta-hydroxybutyrate ester. In some implementations, a ratio of beta-hydroxybutyrate to beta-hydroxy butyrate ester may be approximately 1 beta-hydroxybutyrate salt: approximately 1 beta-hydroxybutyrate ester to approximately 1 beta-hydroxybutyrate salt: approximately 5 beta-hydroxybutyrate ester.

Related compounds that may be included as beta-hydroxybutyrate in the composition may include derivatives of beta-hydroxybutyrate, include esters of (R)-3-hydroxybutyrate and oligomers of (R)-3-hydroxybutyrate. For example, beta-hydroxybutyrate esters derived from alcohols, such as altrose, arabinose, dextrose, erythrose, fructose, galactose, glucose, glycerol, gulose, idose, lactose, lyxose, mannose, ribitol, ribose, ribulose, sucrose, talose, threose, xylitol, xylose, galactosamine, glucosamine, mannosamine, N-acetylglucosamine, mannitol, sorbitol, threitol, (S)-1,2-propanediol and/or (R)-1,3-butanediol. In some implementations, a derivative of the beta-hydroxybutyrate may include structures of (R)-3-hydroxybutyric acid and an exemplary ester thereof (a glycerol monoester). The R chirality of the derivatives may be selected for inclusion in the composition in some implementations (e.g., to deliver R-beta-hydroxybutyrate with the administration of the compound).

In some implementations, butyrate, beta-hydroxybutyrate (e.g., R-beta-hydroxybutyrate), related compounds, and/or combinations thereof may be administered along with one or more additional compounds. The additional compounds may or may not be capable of independently increasing ketone levels, maintaining ketone levels, inducing ketosis, and/or maintaining ketosis. For example, additional compounds capable of independently increasing blood ketone levels may include short chain fatty acids (e.g., fatty acid with between 2 carbons than 6 carbons), short chain triglycerides (e.g., triglycerides with less than 6 carbons), medium chain fatty acids (e.g., fatty acid with 6-12 carbons), medium chain triglycerides (e.g., triglycerides with 7-12 carbons), long chain fatty acids (e.g., fatty acids with more than 12 carbons), long chain triglycerides (e.g., triglycerides with more than 12 carbons), and/or combinations thereof. In some implementations, short chain fatty acids and/or triglycerides may include acetate, propionate, and/or butyrate. Medium chain fatty acids and/or triglycerides may include lauric acid and/or coconut oil, coconut milk powder, fractionated coconut oil, isolated hexanoic acid, isolated octanoic acid, isolated decanoic acid, ethoxylated triglyceride, triglyceride derivatives thereof, aldehyde triglyceride derivatives thereof, monoglyceride derivatives thereof, diglyceride derivatives thereof, triglyceride derivatives thereof, and/or alkyl esters thereof. Long chain fatty acids and/or triglycerides may include dairy products and/or palm oil. In some implementations, a composition including R-beta-hydroxybutyrate and an additional compound that is independently capable of increasing ketone levels may increase ketone levels greater than merely the capability of each component individually (e.g., greater than an additive increase). For example, the composition may include R-beta-hydroxybutyrate and an additional compound independently capable of increasing ketone levels such as caffeine. In some implementations, the composition may include approximately 0.5 g to approximately 50 g of R-beta-hydroxybutyrate and caffeine. In some implementations, the composition may include approximately 0.5 g to approximately 15 g of R-beta-hydroxybutyrate and less than approximately 500 mg of caffeine. In some implementations, the composition may include approximately 0.5 g to approximately 15 g of R-beta-hydroxybutyrate and approximately 5 mg to approximately 500 mg of caffeine. In some implementations, the composition may include approximately 0.5 g to approximately 15 g of R-beta-hydroxybutyrate and approximately 10 mg to approximately 150 mg of caffeine. In some implementations, the composition may include approximately 0.5 g to approximately 15 g of R-beta-hydroxybutyrate and approximately 10 mg to approximately 50 mg of caffeine. The composition with R-beta-hydroxybutyrate (e.g., R-beta-hydroxybutyrate including at least one R-beta-hydroxybutyrate salt) and caffeine may increase and or maintain ketosis, weight loss, fat loss, and/or mental acuity. In some implementations, the composition with R-beta-hydroxybutyrate (e.g., R-beta-hydroxybutyrate including at least one R-beta-hydroxybutyrate salt) and caffeine may increase mental processes (e.g., acuity including cognitive functioning, mood, energy, alertness, focus, performance, effects of aging, etc.); improve and/or maintain body composition; function as a therapeutic for one or more of the described conditions or disorders (e.g., treat neurological disorders); and/or combinations thereof. In some implementations, the composition may include R-beta-hydroxybutyrate and an additional compound independently capable of increasing ketone levels, such as 1,3,7,9-tetramethyluric acid (commercially available as theacrine; and/or commercially available as TeaCrine® from Compound Solutions, California, USA). In some implementations, the composition may include approximately 0.5 g to approximately 15 g of R-beta-hydroxybutyrate and less than approximately 500 mg of 1,3,7,9-Tetramethyluric acid. In some implementations, the composition may include approximately 5 g to approximately 15 g of R-beta-hydroxybutyrate and less than approximately 500 mg of 1,3,7,9-tetramethyluric acid.

For example, a pharmaceutically effective amount of one or more short chain fatty acids and/or one or more short chain triglycerides (e.g., butyric acid and/or butyrate) may be administered with a pharmaceutically effective amount of beta-hydroxybutyrate. In some implementations, approximately 1 g to approximately 10 g of beta-hydroxybutyrate and approximately 0.1 g to approximately 50 g of short chain fatty acid and/or triglyceride may be administered from once a day to approximately 5 times a day. In some implementations, approximately 1 g to approximately 3 g of beta-hydroxybutyrate and approximately 1 g of short chain fatty acid and/or triglyceride may be administered from once a day to approximately 5 times a day. In some implementations, the short chain fatty acid and/or triglyceride may include butyrate or derivatives of butyrate. Butyrate and/or derivatives of butyrate may be administered with and/or without beta-hydroxybutyrate to manage metabolic conditions, such as ketosis, and/or for other appropriate therapeutic purposes. Administered butyrate may be converted to beta-hydroxybutyrate in humans, and thus may increase the amount of beta-hydroxybutyrate delivered to the user. In some implementations, administration of butyrate and beta-hydroxybutyrate may promote hGH synthesis, improve basal and GHRH-induced hGH-secretion, increase muscle fiber cross-sectional area, inhibit intramuscular fat accumulation; reduce fat mass in a user; improve glucose metabolism; increase markers of mitochondrial biogenesis in skeletal muscle and/or whole-body oxygen consumption; reduced markers of oxidative stress and apoptosis and altered antioxidant enzyme activity; cause butyrate enhanced intracellular free cytosolic calcium levels (e.g., by acting through GPR41 and 43); increase beta-hydroxybutyrate levels; and/or support barrier function(s) in the gut and/or reduce inflammation associated with ulcerative colitis. Since butyrate is processed by the body to provide beta-hydroxybutyrate, the delivery of beta-hydroxybutyrate via the butyrate may supplement the directly administered beta-hydroxy butyrate to maintain a level of beta-hydroxybutyrate in the blood (e.g., to promote ketosis, weight loss and/or management, etc.).

However, butyrate and/or butyric acid may not be palatable to individuals (e.g., since the odor and taste are often compared to vomit). Thus, in some implementations, butyrate and/or beta-hydroxybutyrate (e.g., R-beta-hydroxybutyrate) may be processed to reduce organoleptic reactions. For example, the butyrate and/or beta-hydroxybutyrate (e.g., R-beta-hydroxybutyrate) may be encapsulated, microemulsion, liposomes, agglomeration, masking/flavoring technologies, and/or otherwise processed as appropriate to reduce organoleptic reactions from individuals administered the described composition(s). In some implementations, microencapsulated butyrate, beta-hydroxybutyrate, and/or butyric acid may be utilized (e.g., in combination with beta-hydroxybutyrate). Using microencapsulated butyrate, beta-hydroxybutyrate, and/or butyric acid (e.g., when compared with using unencapsulated forms) may increase individual satisfaction and/or compliance with an administration schedule since odor from the butyrate and/or butyric acid may be reduced and/or removed. The microencapsulated butyrate, beta-hydroxybutyrate, and/or butyric acid may be a free-flowing granular powder; dispersible in water; stable in acidic water solution for 30 minutes; allow controlled release in stomach and/or small intestines; inhibit glucose response (e.g., to any added materials); and/or allow delivery of a high butyrate content (e.g., around 70%).

In some implementations, a pharmaceutically effective amount of butyrate may be administered via triglyceride tributyrin (e.g., glyceryl tributyrate or tributyrin). The butyrate via triglyceride tributyrin may be administered separately and/or in conjunction with one or more of the other described compounds (e.g., beta-hydroxybutyrate, fatty acids and/or esters, etc.). For example, up to approximately 200 mg/kg of the individual may be administered (e.g., up to 3 times daily). Administration of the tributyrin may allow a delayed release of butyrate to the body as the tributyrin is processed by the body of the individual. The tributyrin may be unencapsulated and/or encapsulated (e.g., microencapsulated).

In some implementations, administration of beta-hydroxy butyrate and a short chain compound (e.g., short chain fatty acid and/or short chain triglyceride) may unexpectedly increase beta-hydroxybutyrate concentrations in the blood more than the administration of similar amounts of beta-hydroxybutyrate and medium chain compounds (e.g., short chain fatty acid and/or short chain triglyceride) and/or may increase beta-hydroxybutyrate concentrations in the blood more than each component individually.

In some implementations, a pharmaceutically effective amount of beta-hydroxybutyrate may be administered with a pharmaceutically effective amount of long chain fatty acid and/or triglyceride. For example, 0.1-50 g of beta-hydroxybutyrate and 0.1 to 50 g of long chain fatty acid may be administered to an individual between 1-5 times a day. In some implementations, approximately 1 g to approximately 3 g of beta-hydroxybutyrate and approximately 1 g of long chain fatty acid and/or triglyceride may be administered from once a day to approximately 5 times a day.

In some implementations, beta-hydroxybutyrate, short chain compound(s) (e.g., fatty acids and/or triglycerides, butyrate), and/or medium chain compound(s) (e.g., fatty acids and/or triglycerides) may be administered approximately simultaneously and/or sequentially to an individual. For example, approximately 0.1 g to approximately 50 g beta-hydroxybutyrate, approximately 0.1 g to approximately 50 g short chain triglyceride, and approximately 0.1 g to approximately 50 g medium chain fatty acid such as lauric acid and/or coconut oil may be administered between 1-5 times a day. In some implementations, approximately 1 g to approximately 3 g of beta-hydroxy butyrate and approximately 1 g of short chain fatty acid and/or triglyceride and/or approximately 1 g of medium chain fatty acid and/or triglyceride may be administered from once a day to approximately 5 times a day. In some implementations, approximately 0.1 g to approximately 20 g beta-hydroxybutyrate (e.g., salts, esters, isomers, and/or other appropriate forms) may be administered in humans. In some implementations, approximately 0.1 g to approximately 20 g butyrate may be administered in humans.

In some implementations, other compounds, such as compounds capable of independently decreasing glucose levels, may be administered with beta-hydroxybutyrate, such as berberine and/or associated metabolites (e.g., dihydroberberine and/or tetrahydroberberine). U.S. patent application Ser. No. 15/491,933 entitled "ADMINISTRATION OF DIHYDROBERBERINE" to Lowery et al, filed Apr. 19, 2017, and U.S. Provisional Patent Application No. 62/324,794, entitled "ADMINISTRATION OF DIHYDROBERBERINE" to Lowery et al, filed Apr. 19, 2016, describe dihydroberberine administration with ketone sensitizers such as beta-hydroxybutyrate, and is hereby fully incorporated herein. In some implementations, one or more beta-hydroxybutyrates and/or other compounds described herein may be utilized as a ketone sensitizer with the dihydroberberine.

In some implementations, directly administering beta-hydroxybutyrate plus another compound that is processed to deliver beta-hydroxybutyrate (e.g., beta-hydroxybutyrate ester, beta-hydroxybutyrate polymer, butyrate, other appropriate compounds, and/or combinations thereof) over time may allow a first level of beta-hydroxybutyrate in the blood to be maintained over a period of time. For example, since the directly administered beta-hydroxybutyrate may elevate blood beta-hydroxybutyrate levels to a first concentration and this concentration may be approximately maintained over a period of time by providing additional beta-hydroxybutyrate via another compound administered approximately concurrently (e.g., short chain fatty acid and/or triglyceride, beta-hydroxybutyrate ester, beta-hydroxybutyrate polymer, beta-hydroxybutyrate amino acid complex, etc.).

In some implementations, one or more other compounds may be administered (e.g., included in the composition and/or separately administered) with the butyrate (e.g., microencapsulated butyrate), beta-hydroxybutyrate (e.g., R-beta-hydroxybutyrate) and/or fatty acids or esters, such as short chain fatty acids. Other compositions may include, but are not limited to amino acids, amino acid metabolites, vitamins, minerals, coconut milk powder, flavorings, colorings, binders, electrolytes, tetrahydrobiopterin, nucleic acids, alpha-ketoglutaric acid, alpha lipoic acid, nutritional co-factors, beta-methyl-beta-hydroxybutyrate, arginine alpha-ketoglutarate, R-alpha lipoic acid, thiamine, NAD+, NADH, riboflavin, FAD+, FADH, riboflavin-5-phosphate, niacin, nicotinic acid, niacinamide, inositol hexanicotinate, pyridoxine, pyridoxal, pyridoxamine, ascorbic acid and ascorbate salts, citric acid, malic acid, sodium benzoate, pyridoxal-5-phosphate, methylcobalamin, cyanocobalamin, adenosylcobalamin, hydroxycobalamin, pantothenic acid, pantetheine, potassium sorbate, acesulfame K, aspartame, sucralose, stevia, monk fruit extract, allulose, prebiotic fibers, xylo-oligosaccharides (XOS), galacto-oligosaccharides (GOS), mannan-oligosaccharides (MOS), isomaltooligosaccharides (IMO), lipo-oligosaccharides (LOS), xanthan gum, and other organic gums/thickeners/suspension agents, and combinations thereof.

In various implementations, administration of a composition that includes beta-hydroxybutyrate may improve the health of an individual. R-beta-hydroxybutyrate may be capable of providing a greater impact on the health of an individual than D,L-beta-hydroxybutyrate and/or L-beta-hydroxybutyrate. Although previously unknown, L-beta-hydroxybutyrate may decrease the effectiveness of R-beta-hydroxybutyrate with respect to at least a portion of the impact on health. With respect to some impacts on health, L-beta-hydroxybutyrate may have no impact on health. In some implementations, even double the amount of D,L-beta-hydroxybutyrate may not achieve some of the same results (e.g., in health improvement) as R-beta-hydroxybutyrate. Thus, unexpectedly administration of D,L-beta-hydroxybutyrate rather than R-beta-hydroxybutyrate may not have the same impact on health and/or have less of an impact on health of an individual. For example, administration of a composition that includes R-beta-hydroxybutyrate (e.g., and/or other compounds) may improve and/or maintain an individual's health.

Administration of R-beta-hydroxybutyrate as described may increase lifespan in individuals following a dietary plan (e.g., standard American low-fat, ketogenic, Paleo, Mediterranean, etc.) and/or not following a dietary plan. For example, approximately 10 g of R-beta-hydroxybutyrate to approximately 30 g R-beta-hydroxybutyrate may be administered to increase lifespan. In some implementations, other appropriate amounts of R-beta-hydroxybutyrate may be included in the composition.

In some implementations, administration of R-beta-hydroxybutyrate may treat and/or lessen the impact of symptoms of disease(s) and/or disorders, such as diseases that impact cognitive function. Administration of R-beta-hydroxybutyrate may increase motor function in individuals with Parkinson's disease. For example, approximately 5 g of R-beta-hydroxybutyrate to approximately 15 g R-beta-hydroxybutyrate may be administered to increase motor function. In some implementations, other appropriate amounts of R-beta-hydroxybutyrate may be included in the composition.

Administration of R-beta-hydroxybutyrate may increase fat loss. Unlike with conventional diets, in which weight loss often comes from decreases in water retention and/or muscle mass, administration of R-beta-hydroxybutyrate may cause decreases in fat loss (see for example, Figure SB). In addition, administration of R-beta-hydroxybutyrate may decrease levels of LPL in the body, and thus reduce or inhibit fat storage and/or encourage existing fat storage utilization by the body. For example, approximately 1 g of R-beta-hydroxybutyrate to approximately 20 g R-beta-hydroxybutyrate may be administered to cause fat loss and/or reduce fat storage. In some implementations, other appropriate amounts of R-beta-hydroxybutyrate may be included in the composition. Administration of R-beta-hydroxybutyrate may allow fat loss greater than 5 kg while maintaining lean mass. In some implementations, the administration of R-beta-hydroxybutyrate increases the amount of fat used as fuel.

In some implementations, administration of R-beta-hydroxybutyrate may improve and/or maintain health markers such as C-reactive protein and/or fasting glucose. Administration of R-beta-hydroxybutyrate may decrease inflammation (e.g., as shown by C-reactive protein levels). Administration of R-beta-hydroxybutyrate may decrease fasting glucose. For example, approximately 3 g of R-beta-hydroxybutyrate to approximately 20 g R-beta-hydroxybutyrate may be administered to cause a reduction in and/or maintain a low fasting glucose. In some implementations, other appropriate amounts of R-beta-hydroxybutyrate may be included in the composition. In some implementations, R-beta-hydroxybutyrate may be administered with one or more other compounds to decrease glucose levels and/or sensitivity. For example, administration of a composition of R-beta-hydroxybutyrate and a berberine, such as dihydroberberine, may cause, reduce and/or maintain low fasting glucose. Administration of a composition of R-beta-hydroxybutyrate and a berberine, such as dihydroberberine, may cause reduce and/or maintain low glucose levels. In some implementations, less than approximately 15 g of R-beta-hydroxybutyrate may be administered with less than approximately 600 mg of dihydroberberine.

Administration of R-beta-hydroxybutyrate may decrease ketone levels (see e.g., FIGS. 11A and 11B). Decreasing blood ketone levels may increase weight loss, maintain weight loss, improve performance, increase mental acuity, and/or have other health improvement and health maintenance features. For example, even at levels less than 10 g (e.g., approximately 5 g), administration of R-beta-hydroxybutyrate may decrease ketone levels while L-beta-hydroxybutyrate does not, and D,L-beta-hydroxybutyrate does not to the same extent. R-beta-hydroxybutyrate may increase blood ketone levels 5 times as much as similar administration amounts of D,L-beta-hydroxybutyrate. By being able to decrease an amount of R-beta-hydroxybutyrate (e.g., when compared administering D,L-beta-hydroxybutyrate) administered and achieve the same results, a decrease in an amount cation (e.g., sodium, potassium, etc.) may also be administered. Since some individuals may prefer and/or may not tolerate higher dosages of the cations of the R-beta-hydroxybutyrate salt, utilizing R-beta-hydroxybutyrate may allow administration to more people, increase user satisfaction, and/or decrease side effects (e.g., associated with additional consumption of these cations). In some implementations, approximately 0.1 g of R-beta-hydroxybutyrate to approximately 10 g R-beta-hydroxybutyrate may be administered to increase blood ketone levels. Approximately 0.5 g of R-beta-hydroxybutyrate to approximately 3 g R-beta-hydroxybutyrate may be administered to maintain blood ketone levels. In some implementations, other appropriate amounts of R-beta-hydroxybutyrate may be included in the composition.

Administration of R-beta-hydroxybutyrate may increase performance and decrease perceived exertion (e.g., as opposed to when administered D,L-beta-hydroxybutyrate). For example, approximately 3 g of R-beta-hydroxybutyrate to approximately 15 g R-beta-hydroxybutyrate may be administered to increase performance and/or decrease perceived exertion. In some implementations, other appropriate amounts of R-beta-hydroxybutyrate may be included in the composition.

In various implementations, oral administration of R-beta-hydroxybutyrate may increase muscle protein synthesis while D,L-beta-hydroxybutyrate does not increase muscle protein synthesis. For example, approximately 10 g of R-beta-hydroxybutyrate to approximately 30 g R-beta-hydroxybutyrate may be administered to increase muscle protein synthesis. In some implementations, other appropriate amounts of R-beta-hydroxybutyrate may be included in the composition.

Figure 13A:
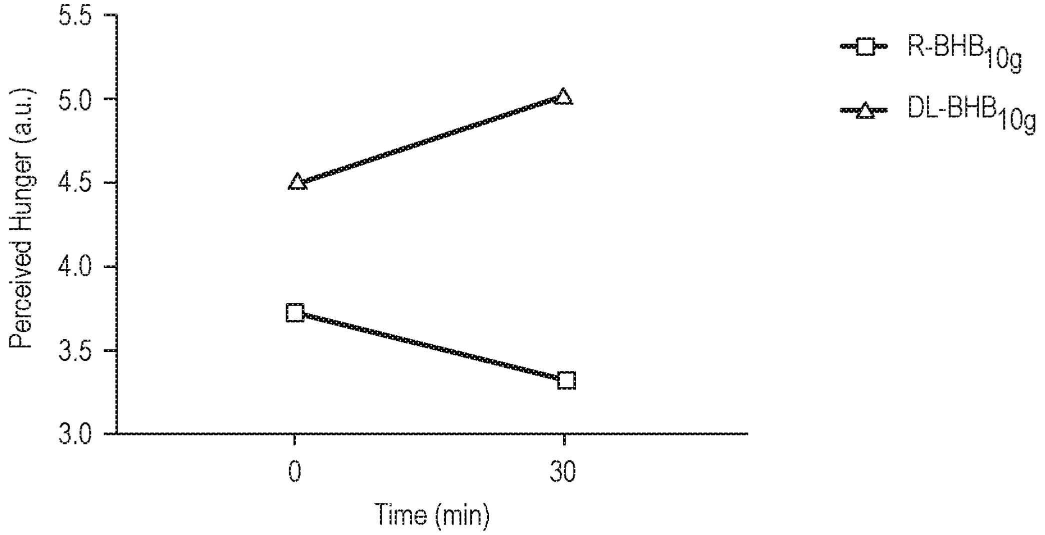
FIG. 13A illustrates a chart illustrating perceived hunger following an implementation of an example administration protocol.
Figure 13B:
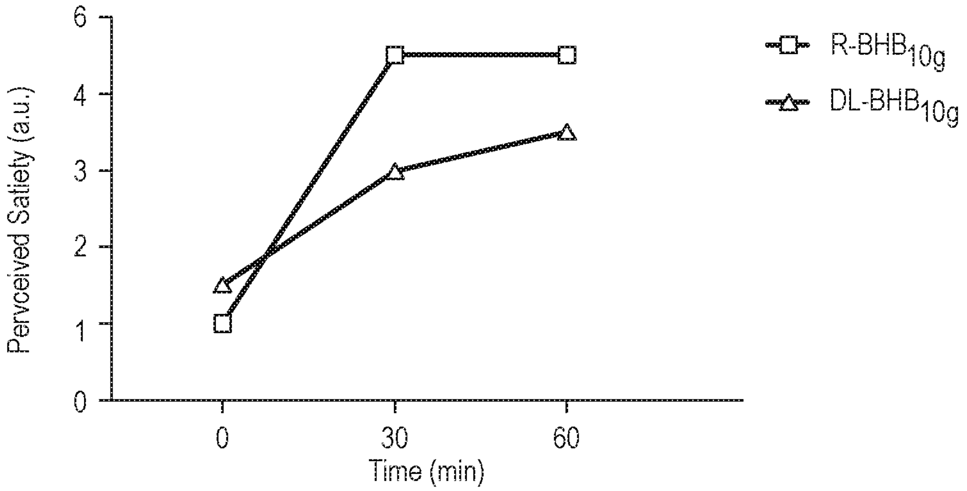
FIG. 13B illustrates a chart illustrating perceived satiety following an implementation of an example administration protocol.

In some implementations, the administration of R-beta-hydroxybutyrate, unlike D,L-beta-hydroxybutyrate may decrease perceived hunger and/or increase satiety) which may inhibit overeating and thus promote weight loss (see e.g., FIGS. 13A and 13B). In some implementations, the administration of R-beta-hydroxybutyrate, unlike D,L-beta-hydroxybutyrate, may increase perceived energy (see e.g., FIG. 13C).

In some implementations, administration of R-beta-hydroxybutyrate increased mental acuity. For example, approximately 0.1 g of R-beta-hydroxybutyrate to approximately 10 g R-beta-hydroxybutyrate may be administered to increase mental acuity. In some implementations, other appropriate amounts of R-beta-hydroxybutyrate may be included in the composition.

In some implementations, the administration of R-beta-hydroxybutyrate may be supplemented with other forms of beta-hydroxybutyrate, butyric acid, and/or butyrate.

In some implementations, the composition administered may include R-beta-hydroxybutyrate. The amount of R-beta-hydroxybutyrate included in the composition may be selected to obtain a result (e.g., induce ketosis; maintain ketosis; increase ketone levels, mental acuity, strength, etc.) upon administration (e.g., a pharmaceutically effective amount may be administered at a dosage and/or over a predetermined time period). In some implementations, the dosage and/or frequency of dosage may vary over time (e.g., initial vs a lower dosage for maintenance, vary based on time of day, vary based on whether taken with or without a meal, etc.).

The R-beta-hydroxybutyrate in the composition may include any appropriate and/or appropriate number of forms, such as salts, derivatives (e.g., esters), polymers, and/or complexes with other compounds. For example, the composition may include R-beta-hydroxybutyrate salt (e.g., sodium R-beta-hydroxybutyrate, magnesium R-beta-hydroxybutyrate, and/or potassium R-beta-hydroxybutyrate) and/or another form of R-beta-hydroxybutyrate (e.g., ester, polymer, complex, etc.). In some implementations, the composition may include an ester of R-beta-hydroxybutyrate. The composition may include an amino acid (e.g., separate and/or complexed with R-beta-hydroxybutyrate), such as leucine. The use of non-salt base R-beta-hydroxybutyrate may increase user satisfaction (e.g., by reducing the cation, such as sodium and/or potassium, load due to ingestion of the composition; by decreasing side effects; etc.), increase the applicability of the administration (e.g., since users sensitive to the cations of the R-beta-hydroxybutyrate salts may be less sensitive to the non-salt and/or lower salt plus non-salt forms of the composition). The administration of the composition may increase blood ketone levels, induce ketosis, maintain blood ketone levels, maintain ketosis, increase health, increase strength, increase mental acuity, etc. In some implementations, a first composition that includes R-beta-hydroxybutyrate salt may be administered to cause a first impact (e.g., induce ketosis, quickly increase mental acuity, quickly increase strength, etc.) and a second composition that includes non-salts R-beta-hydroxybutyrate (e.g., esters, polymers, complexes, etc.) and/or lower levels of R-beta-hydroxybutyrate salt may be utilized to cause a second impact (e.g., maintain ketosis, maintain mental acuity, maintain increased strength, etc.).

In some implementations, the form(s) of R-beta-hydroxybutyrate included in the may be selected based on the delivery form. For example, in some forms of food products the composition may include R-beta-hydroxybutyrate polymer (e.g., due to taste since increased cations like sodium may decrease palatability; due to nutrition since increased cations such as sodium may decrease nutrition; due to mixability, etc.). As another example, the composition may include R-beta-hydroxybutyrate salts or other forms (e.g., microencapsulated) to provide quick-dissolve powders.

In various implementations, a composition may include R-beta-hydroxybutyrate. The R-beta-hydroxybutyrate may be in any appropriate form (e.g., salt, ester, polymer, complex, derivatives thereof, and/or combinations thereof). The composition may include one or more additional compositions. Additional composition(s) may be capable of independently increasing blood ketone levels (e.g., fatty acids or esters, berberine or berberine metabolites such as dihydroberberine, etc.). Additional composition(s) may be capable of independently decreasing blood glucose levels (e.g., berberine or berberine metabolites such as dihydroberberine). In some implementations, additional compounds may not be capable of independently increasing blood ketone levels and/or decreasing blood glucose levels (e.g., additives, flavorings, colorings, minerals, vitamins, binders, anti-caking agents, etc.). The composition may be administered in an effective amount to cause a predetermined health impact (e.g., predetermined level of ketosis, blood ketone level, mental acuity, strength increase, perceived energy, fat loss, weight loss, etc.). The composition may be administered to an individual in a predetermined amount and/or different amounts over an administration schedule. In some implementations, once a first criteria is satisfied (e.g., period of time, number of doses, predetermined health impact), the dosage amount may be altered. For example, first dose(s) of the composition may be administered to cause a predetermined health impact and additional lower dose(s) of the composition may be administered to maintain the predetermined health impact (e.g., caused in part by the first doses).

The composition may be administered in any appropriate delivery form (e.g., tablet; capsule; food products such as powdered products that can be mixed into food, mixed into beverages, and/or consumed directly; beverage product; etc.). The composition may be administered according to any appropriate schedule (e.g., periodic dosages, dosages as user desires, etc.). The administration schedule may inhibit administration that elevates blood ketone levels too high, decreases blood glucose levels too low, and/or causes an individual to consume a dosage that substantially elevates the risk of adverse and/or side effects, in some implementations.

In some implementations, the composition may include a long-acting component and/or be long-acting. For example, since the body digests polymers and/or esters of beta-hydroxybutyrate (e.g., R-beta-hydroxybutyrate), the delivery of R-beta-hydroxybutyrate may be slower than a digestion of a beta-hydroxybutyrate salt (e.g., R-beta-hydroxybutyrate salt). In some implementations, the composition may include a R-beta-hydroxybutyrate and a long acting R-beta-hydroxybutyrate form (e.g., polymer, ester, coated and/or processed form to provide slow release). In some implementations, a first dose(s) may include at least one non-long-acting form of beta-hydroxybutyrate and a second dose(s) may include at least one long-acting form of beta-hydroxybutyrate. The first dose(s) may be administered to cause a predetermined health impact and the second dose(s) may be administered to maintain the caused predetermined health impact. In some implementations, users may select the appropriate dose based on user preference and/or properties (e.g., a user on a ketogenic diet may chose the second dose since the user may already be in ketosis).

EXAMPLES

Example 1

Four (4) subjects were administered 10 g of sodium D,L-beta-hydroxybutyrate and their blood ketone level in mmol/dL was tested after administration, 30 minutes, 60 minutes, 90 minutes, 120 minutes, and 180 minutes after administration. Each subject was also subsequently studied after administration of 10 g of sodium R-beta-hydroxybutyrate and 5 g of sodium R-beta-hydroxybutyrate. As illustrated in FIG. 1, on average, administration of 5 mg of sodium R-beta-hydroxybutyrate produced approximately the same blood ketone level in a subject after 30 minutes, 60 minutes, 90 minutes, 120 minutes, and 180 minutes as 10 g of the sodium D,L-beta-hydroxybutyrate.

Example 2

Three subjects were administered 10 grams of medium chain triglycerides and 8 grams of beta-hydroxybutyrate and blood beta-hydroxybutyrate concentration was monitored over time. The same subjects were later administered 10 grams of short chain triglycerides and 8 grams of beta-hydroxy butyrate and blood beta-hydroxy butyrate concentration was monitored. FIG. 2 illustrates an average blood ketone concentration (mmol/L) for the subjects after administration, after 30 minutes, after 60 minutes, after 90 minutes, after 120 minutes, and after 180 minutes. As illustrated in FIG. 2, administration of the beta-hydroxybutyrate with a short chain compound (illustrated in black bars or the second bar in each set), such as short chain triglyceride, caused greater elevation of blood ketone levels than administration of a similar amount of medium chain compound (illustrated in the blue bars or first bar in each set) at least after administration, after 30, 60, 90 minutes, and 180 minutes. Thus, administration of short chain compounds (e.g., fatty acids and/or triglycerides) may unexpectedly allow a smaller weight amount, when compared to medium chain compounds, to be administered to produce the same result (e.g., blood ketone level, weight loss, weight management, etc.) and/or allow greater results (e.g., when compared with similar amount of medium chain compounds).

Example 3

Figure 3:
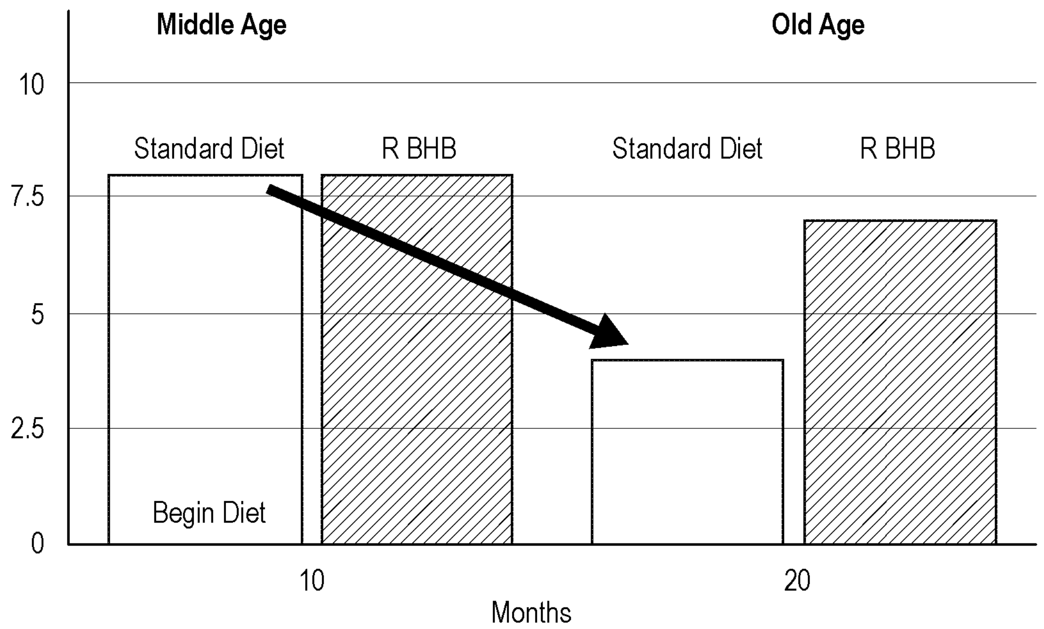
FIG. 3 illustrates a chart including lifespan of rats subject to an implementation of an administration of R-beta-hydroxybutyrate.

Sixteen rats (Fischer 344 rats) were studied for the effect of R-beta-hydroxybutyrate on lifespan. A first grouping of eight rats were fed an equivalent to a low-fat standard American diet and a second grouping of eight rats were fed the same equivalent to a low-fat standard American diet and supplemented with R-beta-hydroxybutyrate salt (e.g., sodium R-beta-hydroxybutyrate). The second grouping of rats were supplemented with the R-beta-hydroxybutyrate salt at middle age. FIG. 3 illustrates the average lifespans of the groupings of rats. As illustrated, at 20 months approximately half of the first grouping of rats died on the standard diet while only 12.5% of the second grouping of rats had died at 20 months. Thus, the supplementation of rat diets with R-beta-hydroxybutyrate increased lifespan in at least approximately 38.5% of the rats. Since the rat study was performed as an approximation of impact in humans, the addition of R-beta-hydroxybutyrate to a standard American low-fat diet may increase lifespan.

Example 4

An individual with Parkinson's disease was tested for motor function with and without administration of approximately 10 g of R-beta-hydroxybutyrate salt. The testing included a right-eye visual and motor performance apparatus to track motor function through eye movements.

Figure 4:
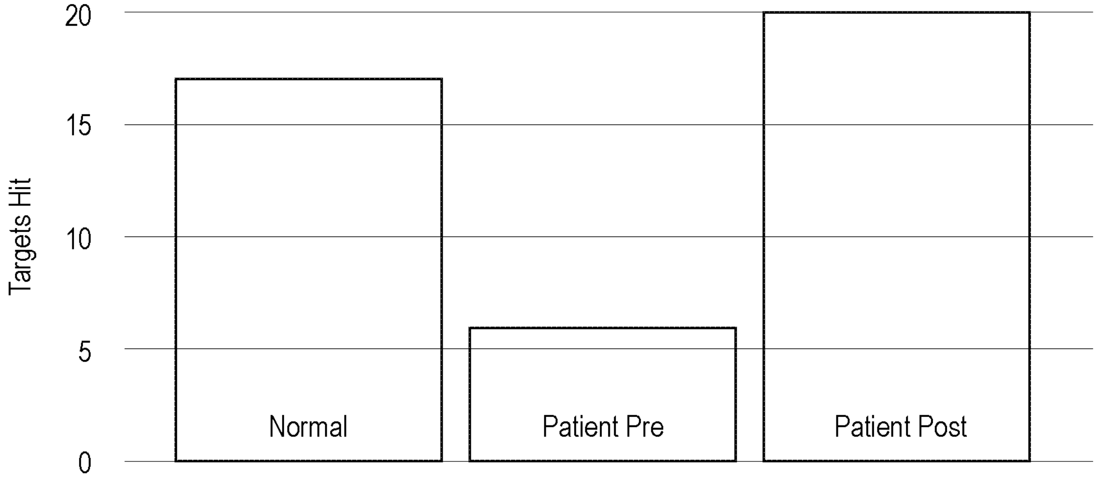
FIG. 4 illustrates a chart illustrating the results of motor skill testing following an implementation of an example administration protocol.

FIG. 4 is a chart illustrating the results of the motor skill testing following an example implementation of administration of R-beta-hydroxybutyrate. FIG. 4 illustrates average results for a similar non-Parkinson's population, the patient pre-administration of R-beta-hydroxybutyrate, and the patient post-administration of R-beta-hydroxybutyrate. As illustrated, the administration of R-beta-hydroxybutyrate increased motor function (e.g., approximately 30 minutes after administration of the R-beta-hydroxybutyrate).

Example 5

Figures 5A, 5B:
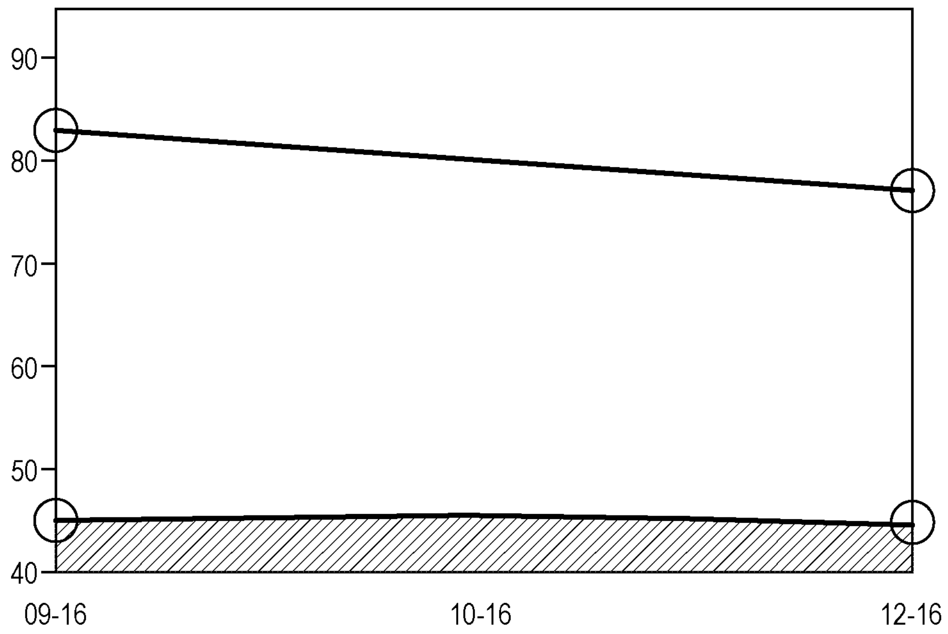
FIG. 5A illustrates a chart illustrating fat loss results following an implementation of an example administration protocol.
FIG. 5B illustrates a chart illustrating fat mass and lean mass results following an implementation of an example administration protocol.

An individual was administered 5 g of R-beta-hydroxybutyrate twice daily for 3 months. Xray absorptiometry was performed to determine the impact of the administration of R-beta-hydroxybutyrate on fat loss. FIG. 5A illustrates a chart that shows the results after 3 months of administration. As illustrated, the individual experienced a greater than approximately 10% decrease in fat mass. FIG. 5B illustrates that the fat loss was sustained while maintaining lean mass. Thus, the R-beta-hydroxybutyrate may cause weight loss through fat loss rather than lean mass (e.g., muscle mass).

Example 6

Figure 6:
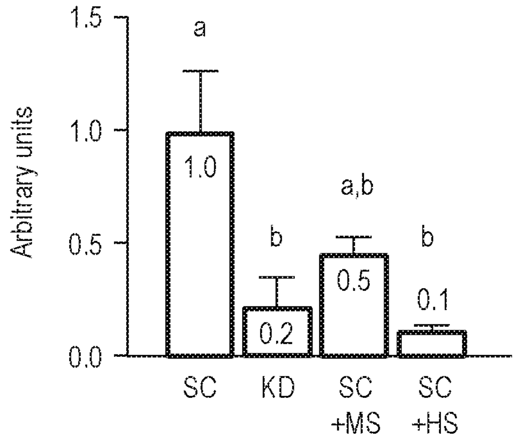
FIG. 6 illustrates a chart illustrating LPL levels in rats following an implementation of an example administration protocol.

A first grouping of 10 rats (labeled SC) were given a standard diet, a second grouping of 10 rats (labeled KD) were given a ketogenic diet, a third grouping of 10 rats (labeled SC+MS) were on the standard diet but given a first dosage of R-beta-hydroxybutyrate salt (e.g., equivalent to 5 g) and a fourth grouping was on the standard iet but given a second dosage of R-beta-hydroxybutyrate salt (e.g., equivalent to 10 g). FIG. 6 illustrates the average Lipoprotien lipase (LPL) in the rats. Since LPL is needed to transport fat into adipose tissue, lowering LPL levels would inhibit fat storage and encourage usage of fat storages. As illustrated, supplementation of a standard diet with even lower dosages of R-beta-hydroxybutyrate decreases LPL levels and thus inhibits fat storage.

Example 7

An individual with high C-reactive protein, which is associated with inflammation, was administered R-beta-hydroxybutyrate. After administration, the C-reactive protein levels were substantially reduced (e.g., 62.5 to 4.4). In addition, fasting glucose was decreased (e.g., 104 to 95).

Example 8

Figure 7:
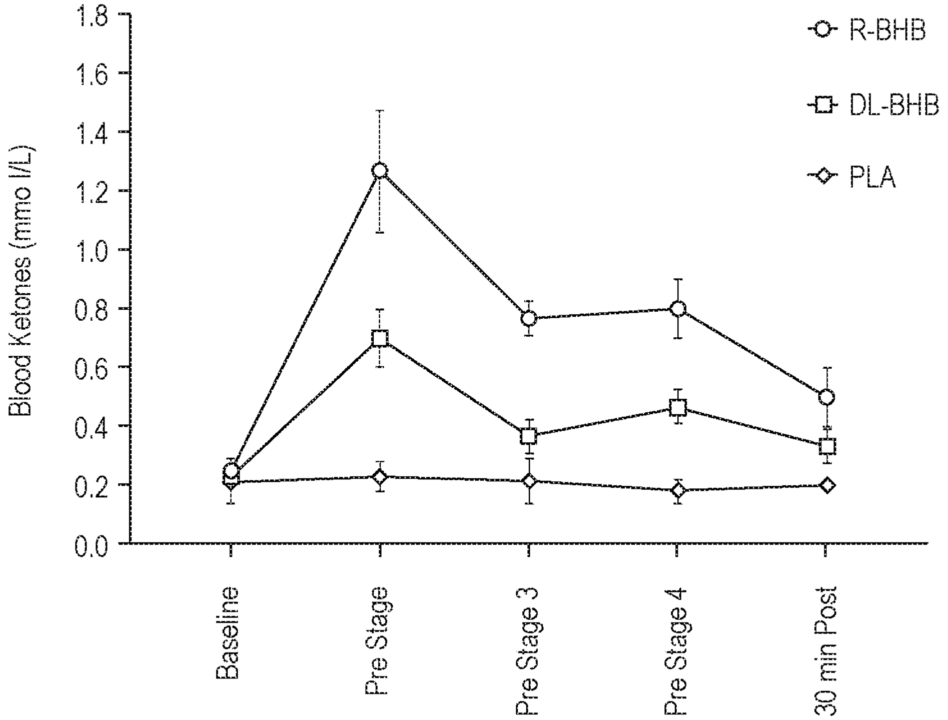
FIG. 7 illustrates a chart illustrating blood ketone levels following an implementation of an example administration protocol.
Figure 8:
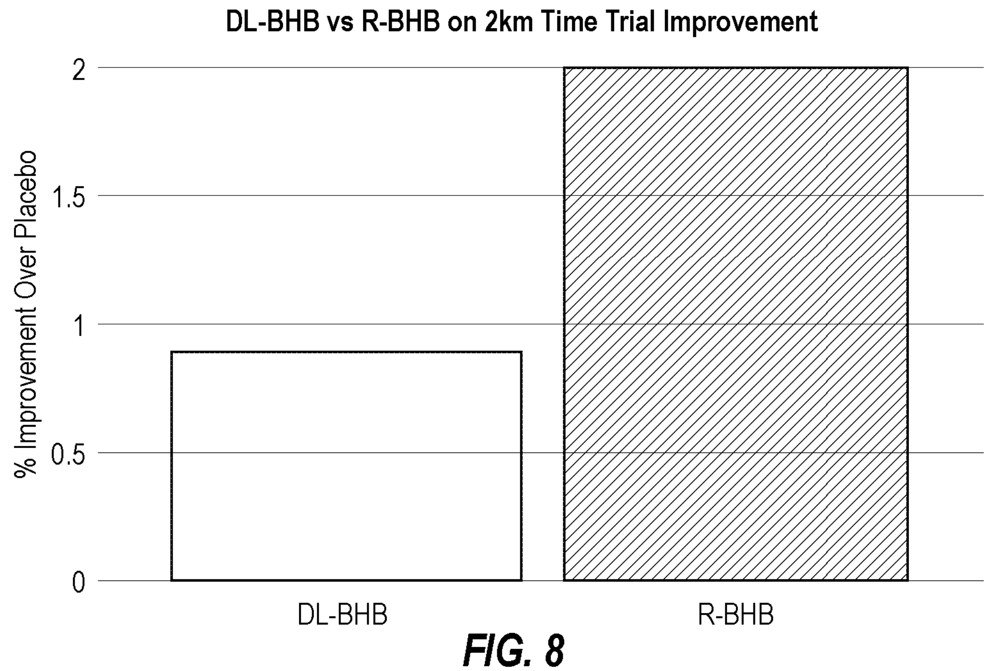
FIG. 8 illustrates a chart illustrating improvement over a placebo following an implementation of an example administration protocol.
Figure 9:
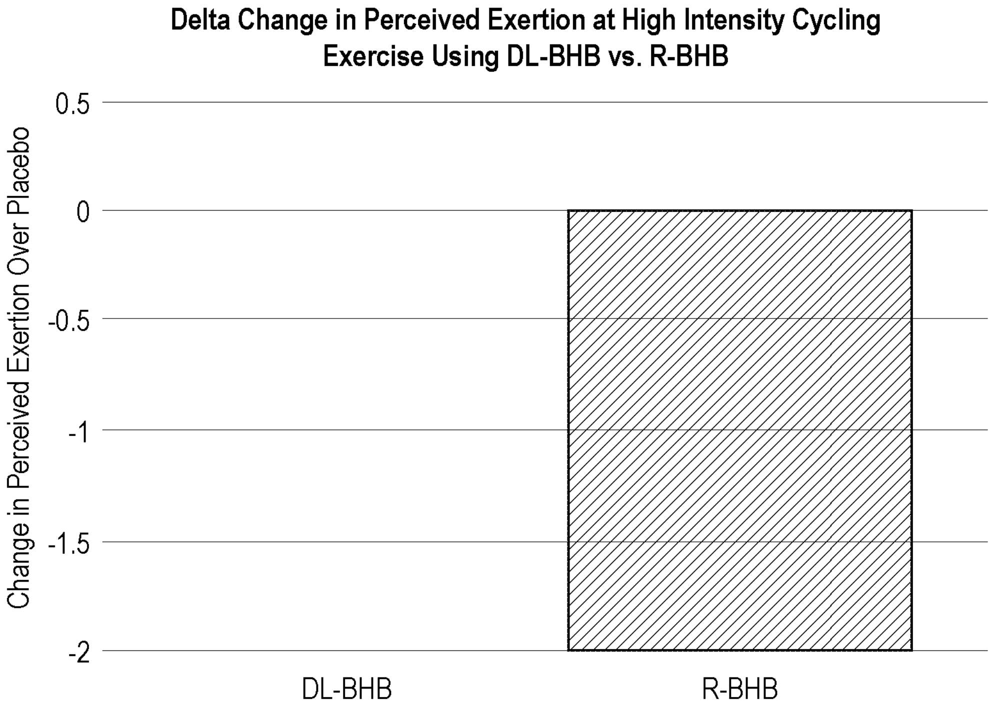
FIG. 9 illustrates a chart illustrating perceived exertion following an implementation of an example administration protocol.

Five healthy individuals were given a 2 km time test (e.g., 4 cycles of low to severely intense exercise on a wingate cycle ergometer) 30 minutes after administration of a placebo, 10 g of R-beta-hydroxybutyrate, and 10 g of R-beta-hydroxybutyrate. FIG. 7 illustrates the average blood ketone levels and FIG. 8 illustrates the percentage improvement over the administration of the placebo. As illustrated, blood ketone levels unexpectedly increased more than double during administration of R-beta-hydroxybutyrate when compared with administration of D,L-beta-hydroxybutyrate. In addition, performance (e.g., improvement in time) increased by more than double during administration of R-beta-hydroxybutyrate when compared with D,L-beta-hydroxybutyrate. FIG. 9 illustrates the perceived exertion experienced by the individuals. As illustrated, the individuals did not feel an impact in perceived exertion after administration with D,L-beta-hydroxybutyrate as compared with the perceived exertion improvement experienced after administration of R-beta-hydroxybutyrate. Thus, the R-beta-hydroxybutyrate has an unexpected impact on ketone levels and performance.

Example 9

Individuals were given a standard diet or ketogenic diet. Some individuals were administered R-beta-hydroxybutyrate (e.g., 10 g). R-beta-hydroxybutyrate was able to numerically increase superoxide dismutase 2 levels (SOD) in the brain which indicates greater antioxidant capacity in the brain.

Example 10

Figure 10:
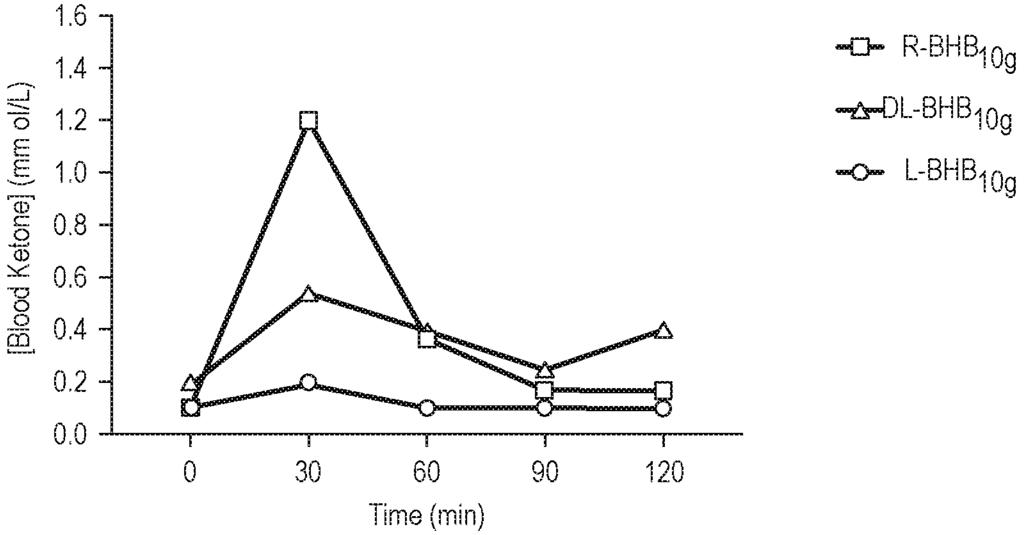
FIG. 10 illustrates a chart illustrating blood ketone levels following an implementation of an example administration protocol.
Figure 11:
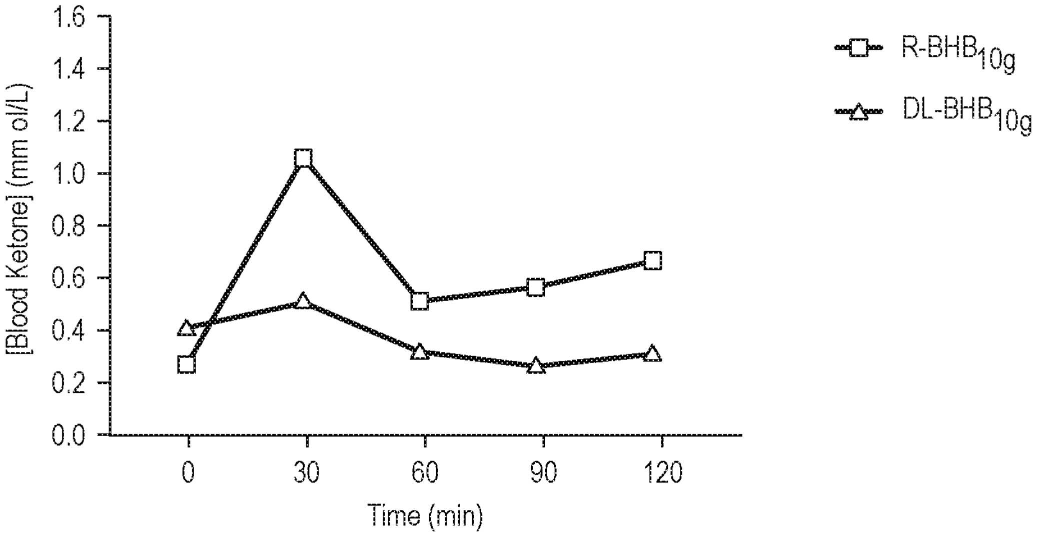
FIG. 11 illustrates a chart illustrating blood ketone levels following an implementation of an example administration protocol.

Individuals were 5 g or 10 mg of R-beta-hydroxybutyrate, L-beta-hydroxybutyrate, or D,L-beta-hydroxybutyrate and blood ketone levels were measured. FIGS. 10 and 11 illustrate the measured blood ketone levels. As illustrated, administration of R-beta-hydroxybutyrate may decrease ketone levels (see e.g., FIGS. 11A and 11B). The reduction of ketone levels occurs even when R-beta-hydroxybutyrate is administered at a dosage of less than 10 g (e.g., approximately 5 g). In addition, unexpectedly (e.g., since it was expected that both the D and L forms of R-beta-hydroxybutyrate behaved in a similar manner), administration of L-beta-hydroxybutyrate does not decrease blood ketones. Furthermore, unexpectedly, even D,L-beta-hydroxybutyrate does not lower blood ketone levels to the same extent as R-beta-hydroxybutyrate. This indicates that L-beta-hydroxybutyrate may block some of the impact of R-beta-hydroxybutyrate, which is unexpected.

Example 11

Figure 12A:
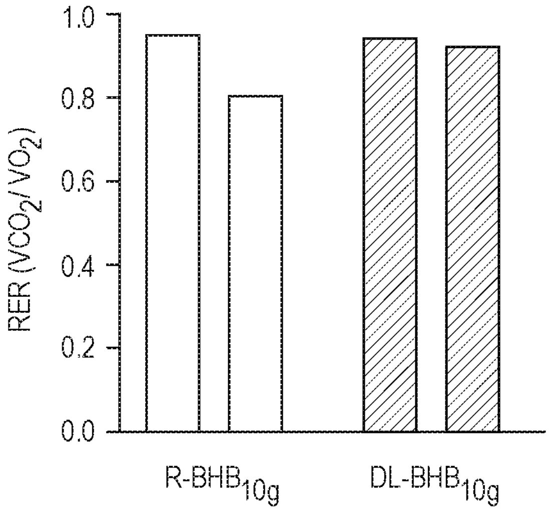
FIG. 12A illustrates a chart illustrating RER levels following an implementation of an example administration protocol.
Figure 12B:
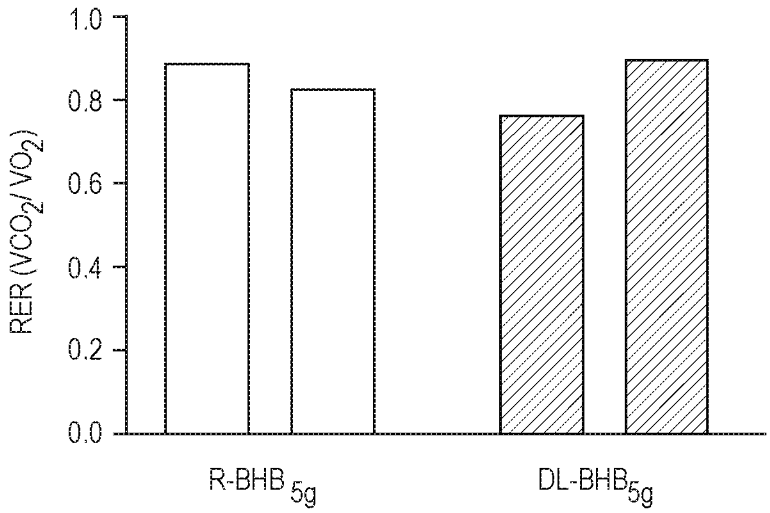
FIG. 12B illustrates a chart illustrating RER levels following an implementation of an example administration protocol.

10 subjects were administered approximately 5 g or 10 g of D,L-beta-hydroxybutyrate or R-beta-hydroxybutyrate, and respiratory exchange ratio was examined (RER, a ratio of carbon dioxide/oxygen). Generally, a ratio of 1.0 indicates that 100% carbohydrate is used as fuel and at 0.7, 100% fat is used as fuel. As illustrated in FIG. 12A, at 10 g, R-beta-hydroxybutyrate administration reduces RER approximately 3 times more than D,L-beta-hydroxybutyrate. As illustrated in FIG. 12B, 5 g of R-beta-hydroxybutyrate is capable of achieving a result that even more D,L-beta-hydroxybutyrate is unable to (e.g., D,L-beta-hydroxybutyrate increases RER by 17% rather than decreasing RER).

Example 12

Figure 13C:
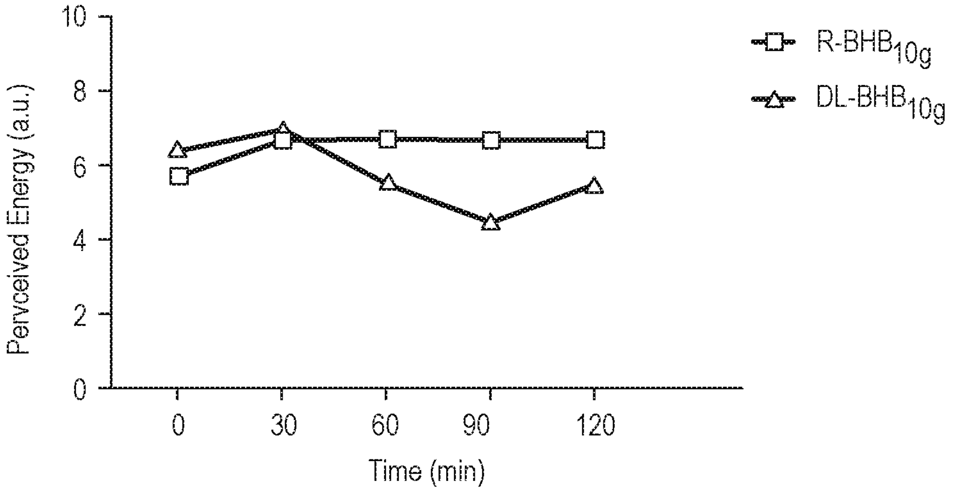
FIG. 13C illustrates a chart illustrating perceived energy following an implementation of an example administration protocol.

Individuals were administered 5 g-10 g of D,L-beta-hydroxybutyrate or R-beta-hydroxybutyrate and tested for perceived hunger, satiety, and perceived energy. FIGS. 13A-13C illustrate the results of the testing. FIG. 13A illustrates perceived hunger, FIG. 13B illustrates perceived satiety, and FIG. 13C illustrates perceived energy. As illustrated in FIG. 13B, at 30 minutes post consumption R-beta-hydroxybutyrate improved satiety levels 2.3 times better than DL-beta-hydroxybutyrate relative to baseline levels. As illustrated in FIG. 13C, R-beta-hydroxybutyrate improved perceived energy from O to 30 minutes post consumption by double that of D,L-beta-hydroxybutyrate. R-beta-hydroxybutyrate sustained elevated perceived energy levels from O minutes at 60, 90, and 120 minutes post consumption, as opposed to D,L-beta-hydroxybutyrate. As illustrated, R-beta-hydroxybutyrate was able to raise perceived energy by 18% and sustain it for 2 hours post ingestion (e.g., more than 2 times greater than the peak value of increase with the DL-beta-hydroxybutyrate)

Example 13

Figure 14A:
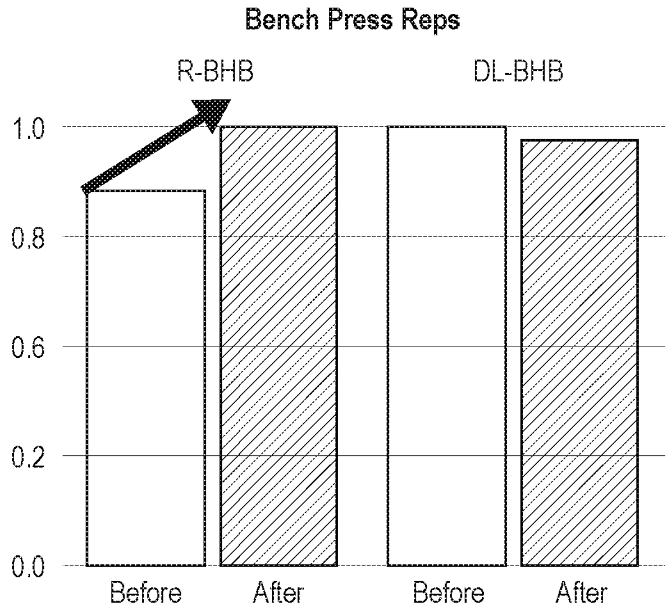
FIG. 14A illustrates a chart illustrating strength test results following an implementation of an example administration protocol.
Figure 14B:
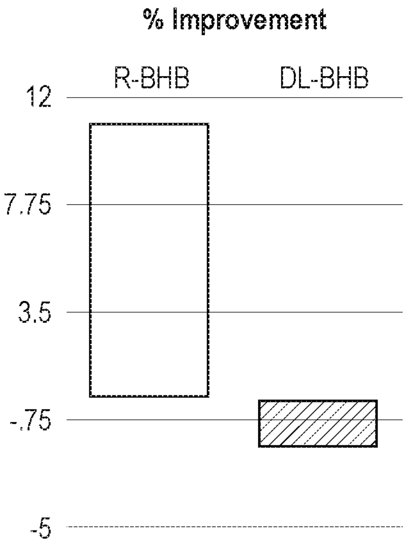
FIG. 14B illustrates a chart illustrating strength test results following an implementation of an example administration protocol.

Five (5) young (20s) resistance trained males lifting 50% of their 1-RM on Bench Presses were tested before and after administration of 5 g of R-beta-hydroxybutyrate or D,L-beta-hydroxybutyrate. FIGS. 14A-B illustrate the results of the testing. As illustrated, R-beta-hydroxybutyrate administration resulted in an 11% increase, while DL-beta-hydroxybutyrate administration resulted in a 2% decrease. Thus, R-beta-hydroxybutyrate experienced a greater than expected impact when compared with D,L-beta-hydroxybutyrate.

Figure 14C:
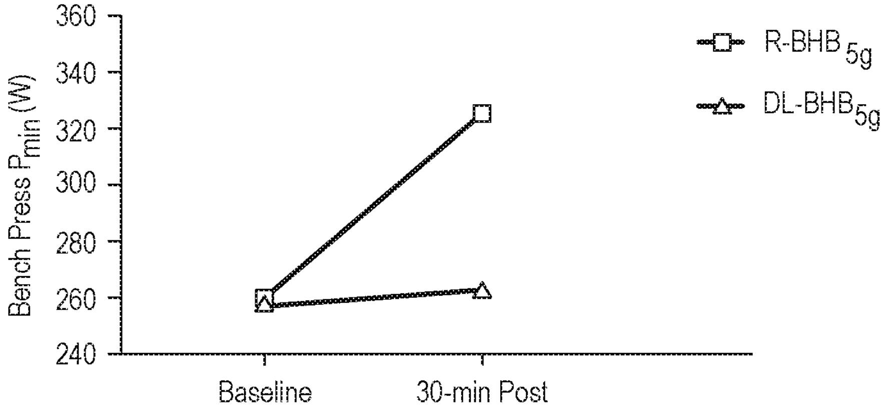
FIG. 14C illustrates a chart illustrating power test results following an implementation of an example administration protocol.

The individuals were also tested for power. FIG. 14C illustrates the results of the testing (e.g., averages of power measurements). As illustrated, R-beta-hydroxybutyrate administration increased minimum power by 26%, while the DL-beta-hydroxybutyrate administration raised power by 2%.

Example 14

Individuals were tested for mental acuity before and after administration of 5-10 g of R-beta-hydroxybutyrate or D,L-beta-hydroxybutyrate. Circular Tracking testing (e.g., to assess their cognitive function) was performed and administration of DL-beta-hydroxybutyrate (e.g., 10 g) caused no improvement while the R-beta-hydroxybutyrate (e.g., 10 g) administration caused approximately 3% improvement in tracking accuracy. Vertical Tracking testing (e.g., to assess their cognitive function) was performed and administration of D,L-beta-hydroxybutyrate (e.g., 10 g) improved performance by 4.6%, while the administration of R-beta-hydroxybutyrate (e.g., 10 g) improved performance by 13.8%, which is approximately 3 times greater improvement. Horizontal Saccades testing was performed (e.g., a saccade is one eye movement and known to become significantly slower if cognitive function declines and improve if cognitive function improves). In the horizontal saccades testing, performance improvements were 4 times greater with the administration of R-beta-hydroxybutyrate (e.g., 5 g) than with administration of D,L-beta-hydroxybutyrate (e.g., 13.8% vs. 3.2%). Processing speed testing was performed (e.g., processing speed is considered a true measure of cognitive performance). Administration of R-beta-hydroxybutyrate (e.g., 5 g) improved processing speed by 27.7% and only approximately 18% with administration of the DL-beta-hydroxybutyrate (e.g., 5 g). Response accuracy was also tested. Administration of R-beta-hydroxybutyrate (e.g., 5 g) increased accuracy by 37 percentage points when compared to 12.7% when D,L-beta-hydroxybutyrate was administered.

Thus, administration of R-beta-hydroxybutyrate increased mental acuity more than a similar amount of D,L-beta-hydroxybutyrate. In fact, as the testing revealed, the administration of R-beta-hydroxybutyrate increased mental acuity often by than double when compared with a similar amount of D,L-beta-hydroxybutyrate.

Example 15

Figure 15:
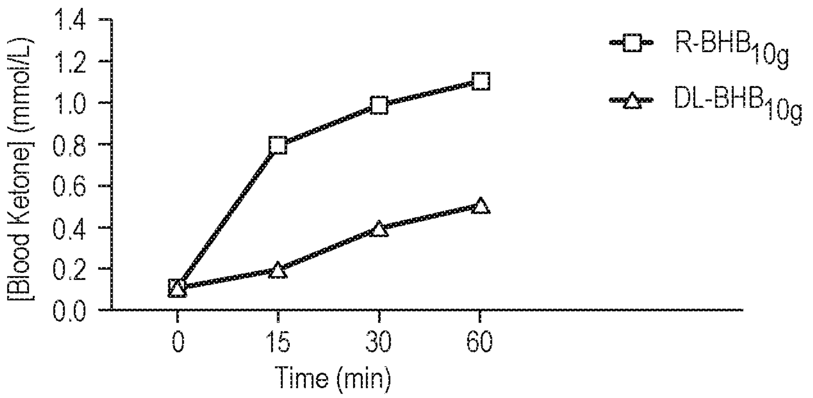
FIG. 15 illustrates a chart illustrating blood ketone levels following an implementation of an example administration protocol.

The compound for administration was prepared to include an R-beta-hydroxybutyrate amino acid complex. An R-beta-hydroxybutyrate Agmatine complex was prepared and an R-beta-hydroxybutyrate Arginine complex was prepared. FIG. 15 illustrates the average blood ketone levels achieved with the R-beta-hydroxybutyrate amino acid complex (e.g., an average of both complexes) when compared with D,L-beta-hydroxybutyrate. As illustrated, blood ketone levels are not only more than double the blood ketone levels achieved with the same quantity of D,L-beta-hydroxybutyrate as R-beta-hydroxybutyrate amino acid complex (e.g., 10 g), but they are more than an additive result of a similar amount of R-beta-hydroxybutyrate and amino acid.

Use of the R-beta-hydroxybutyrate amino acid complex may reduce the amount of cation delivered (e.g. since the complex may deliver the R-beta-hydroxybutyrate rather than a R-beta-hydroxybutyrate salt). The reduction of this cation may decrease side effects (e.g., from increased sodium, potassium, and/or magnesium intake), increase user satisfaction, and/or increase the population that can tolerate the administration of R-beta-hydroxybutyrate (e.g., since some individuals may not be capable of increasing loads of these cations due to underlying diseases and/or disorder). The use of the R-beta-hydroxybutyrate amino acid complex may also allow a higher yield of R-beta-hydroxybutyrate to be administered (90.8% R-beta-hydroxybutyrate, 5% amino acid) when compared with a similar weight of R-beta-hydroxybutyrate salt (e.g., average of 83% yield for BHB sodium).

Example 16

Figure 16:
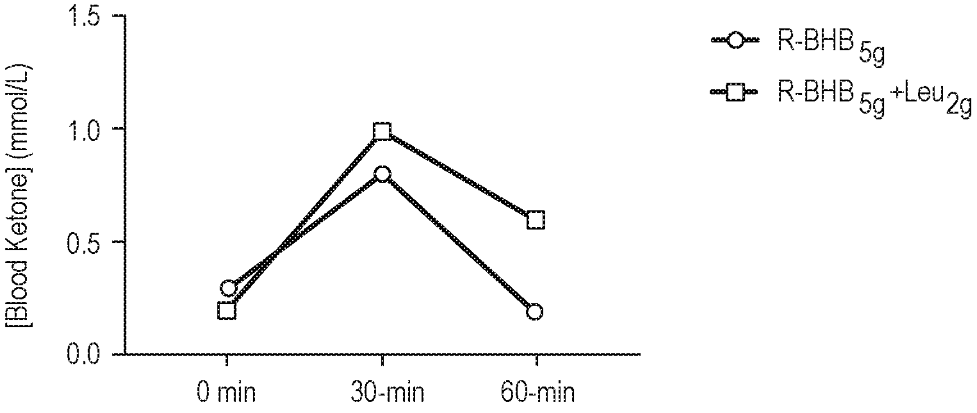
FIG. 16 illustrates a chart illustrating blood ketone levels following an implementation of an example administration protocol.

A composition for administration may include R-beta-hydroxybutyrate and an amino acid, such as leucine. The R-beta-hydroxybutyrate and leucine may be complexed and/or mixed together for administration. The R-beta-hydroxybutyrate and leucine may be administered separately but approximately concurrently. FIG. 16 illustrates the blood ketone levels after administration of R-beta-hydroxybutyrate (5 g) and leucine (2 g). As illustrated, the administration of R-beta-hydroxybutyrate and leucine causes greater elevation of blood ketone levels than the administration of R-beta-hydroxybutyrate (5 g). The administration of R-beta-hydroxybutyrate and leucine causes greater elevation of blood ketone levels than merely the additive effect of similar quantities of R-beta-hydroxybutyrate and leucine administered separately.

Example 17

An aqueous beta-hydroxybutyric acid solution is prepared by mixing beta-hydroxybutyric acid (e.g., powder or other solid form) with water to form a highly concentrated solution containing 60% w/v of beta-hydroxybutyric acid. The concentrated aqueous beta-hydroxybutyric acid solution is readily administered as a ketogenic composition by mixing with 10 to 30 parts of water, juice, beverage, or other aqueous composition.

Example 18

An aqueous beta-hydroxybutyric acid solution is prepared by mixing beta-hydroxybutyric acid (e.g., powder or other solid form) with water to form a highly concentrated solution containing 50% w/v of beta-hydroxybutyric acid. The concentrated aqueous beta-hydroxybutyric acid solution is readily administered as a ketogenic composition by mixing with 9 to 28 parts of water, juice, beverage, or other aqueous composition.

Example 19

An aqueous beta-hydroxybutyric acid solution is prepared by mixing beta-hydroxybutyric acid (e.g., powder or other solid form or more concentrated solution) with water to form a less highly concentrated solution containing 40% w/v of beta-hydroxybutyric acid. The concentrated aqueous beta-hydroxybutyric acid solution is readily administered as a ketogenic composition by mixing with 8 to 25 parts of water, juice, beverage, or other aqueous composition.

Example 20

An aqueous beta-hydroxybutyric acid solution is prepared by mixing beta-hydroxybutyric acid (e.g., powder or other solid form or more concentrated solution) with water to form a less highly concentrated solution containing 35% w/v of beta-hydroxybutyric acid. The concentrated aqueous beta-hydroxybutyric acid solution is readily administered as a ketogenic composition by mixing with 7 to 22 parts of water, juice, beverage, or other aqueous composition.

Example 21

An aqueous beta-hydroxybutyric acid solution is prepared by mixing beta-hydroxybutyric acid (e.g., powder or other solid form or more concentrated solution) with water to form a moderately concentrated solution containing 30% w/v of beta-hydroxybutyric acid. The concentrated aqueous beta-hydroxybutyric acid solution is readily administered as a ketogenic composition by mixing with 6 to 18 parts of water, juice, beverage, or other aqueous composition.

Example 22

An aqueous beta-hydroxybutyric acid solution is prepared by mixing beta-hydroxybutyric acid (e.g., powder or other solid form or more concentrated solution) with water to form a moderately concentrated solution containing 25% w/v of beta-hydroxybutyric acid. The concentrated aqueous beta-hydroxybutyric acid solution is readily administered as a ketogenic composition by mixing with 5 to 15 parts of water, juice, beverage, or other aqueous composition.

Example 23

An aqueous beta-hydroxybutyric acid solution is prepared by mixing beta-hydroxybutyric acid (e.g., powder or other solid form or more concentrated solution) with water to form a moderately concentrated solution containing 20% w/v of beta-hydroxybutyric acid. The concentrated aqueous beta-hydroxybutyric acid solution is readily administered as a ketogenic composition by mixing with 4 to 12 parts of water, juice, beverage, or other aqueous composition.

Example 24

An aqueous beta-hydroxybutyric acid solution is prepared by mixing beta-hydroxybutyric acid (e.g., powder or other solid form or more concentrated solution) with water to form a fairly concentrated solution containing 15% w/v of beta-hydroxybutyric acid. The concentrated aqueous beta-hydroxybutyric acid solution is readily administered as a ketogenic composition by mixing with 3 to 9 parts of water, juice, beverage, or other aqueous composition.

Example 25

An aqueous beta-hydroxybutyric acid solution is prepared by mixing beta-hydroxybutyric acid (e.g., powder or other solid form or more concentrated solution) with water to form a fairly concentrated solution containing 10% w/v of beta-hydroxybutyric acid. The concentrated aqueous beta-hydroxybutyric acid solution is readily administered as a ketogenic composition by mixing with 2 to 8 parts of water, juice, beverage, or other aqueous composition.

Example 26

An aqueous beta-hydroxybutyric acid solution is prepared by mixing beta-hydroxybutyric acid (e.g., powder or other solid form or more concentrated solution) with water to form a fairly dilute solution containing 6% w/v of beta-hydroxybutyric acid. The aqueous beta-hydroxybutyric acid solution can be used as is or mixed with another substance.

Example 27

An aqueous beta-hydroxybutyric acid solution is prepared by mixing beta-hydroxybutyric acid (e.g., powder or other solid form or more concentrated solution) with water to form a fairly dilute solution containing 5% w/v of beta-hydroxybutyric acid. The aqueous beta-hydroxybutyric acid solution can be used as is or mixed with another substance.

Example 28

An aqueous beta-hydroxybutyric acid solution is prepared by mixing beta-hydroxybutyric acid (e.g., powder or other solid form or more concentrated solution) with water to form a moderately dilute solution containing 4% w/v of beta-hydroxybutyric acid. The aqueous beta-hydroxybutyric acid solution can be used as is or mixed with another substance.

Example 29

An aqueous beta-hydroxybutyric acid solution is prepared by mixing beta-hydroxybutyric acid (e.g., powder or other solid form or more concentrated solution) with water to form a more dilute solution containing 3% w/v of beta-hydroxybutyric acid. The aqueous beta-hydroxybutyric acid solution can be used as is or mixed with another substance.

Example 30

An aqueous beta-hydroxybutyric acid solution is prepared by mixing beta-hydroxybutyric acid (e.g., powder or other solid form or more concentrated solution) with water to form an even more dilute solution containing 2% w/v of beta-hydroxybutyric acid. The aqueous beta-hydroxybutyric acid solution can be used as is or mixed with another substance.

Example 31

An aqueous beta-hydroxybutyric acid solution is prepared by mixing beta-hydroxybutyric acid (e.g., powder or other solid form or more concentrated solution) with water to form a very dilute solution containing 1.5% w/v of beta-hydroxybutyric acid. The aqueous beta-hydroxybutyric acid solution can be used as is or mixed with another substance.

Example 32

An aqueous beta-hydroxybutyric acid solution is prepared by mixing beta-hydroxybutyric acid (e.g., powder or other solid form or more concentrated solution) with water to form a highly dilute solution containing 1% w/v of beta-hydroxybutyric acid. The aqueous beta-hydroxybutyric acid solution can be used as is or mixed with another substance.

Example 33

Any of the foregoing aqueous beta-hydroxybutyric acid solutions of Examples 17-32 is modified by including a gelling agent to form a gel. The gelling agent can be one or more of gellan gum, pectin, agar, carrageenan, xanthan gum, alginate, starch, modified starch, gum Arabic, guar gum, locust bean gum, konjac maanan, gum tragacanth, acacia gum, gum karaya, methyl cellulose, agar, pullulan, konjac, hydroxypropylmethyl cellulose, other cellulosic compounds, other polysaccharide gums, gelatin, collagen, casein, other proteins, silica fume, milled chia seeds, and other hydrocolloids. The gelling agent is included in an amount to yield a gel of desired consistency, such as a viscous Newtonian fluid or a Bingham plastic.

Example 34

Any of the foregoing beta-hydroxybutyric acid solutions or gels of Examples 17-33 includes other carrier materials in which beta-hydroxybutyric acid is insoluble or less soluble in order to form a suspension containing particles of beta-hydroxybutyric acid. In some cases the quantity of water is reduced to be less than the amount required to dissolve the beta-hydroxybutyric acid. The suspension can be a liquid, a gel, a sauce, or other food or drink material.

Example 35

Any of the foregoing beta-hydroxybutyric acid compositions of Examples 17-34 is combined with one or more short chain fatty acids or ester thereof.

Example 36

Any of the foregoing beta-hydroxybutyric acid compositions of Examples 17-35 is combined with a beta-hydroxybutyrate compound containing a cationic amino acid selected from arginine, lysine, leucine, iso-leucine, histidine, ornithine, citrulline, L-glutamine, or metabolite of an amino acid, such as creatine). The beta-hydroxybutyrate amino acid compound provides an additional source of beta-hydroxybutyrate without adding electrolytes to the composition.

Example 37

Any of the foregoing beta-hydroxybutyric acid compositions of Examples 17-36 can include a non-racemic mixture enriched with R-beta-hydroxybutyric acid, which can be prepared by mixing R-beta-hydroxybutyric acid with a racemic mixture of R- and S-beta-hydroxybutyric acids to provide greater than 50% and less than 100% by enantiomeric equivalents of R-beta-hydroxybutyric acid and less than 50% and greater than 0% by enantiomeric equivalents of S-beta-hydroxybutyric acid. Because the non-racemic mixture includes more of the R-enantiomer, the onset of ketosis is accelerated for a given dosage as compared to the same dosage of a racemic mixture. On the other hand, including the S-enantiomer provides for a longer state of ketosis and/or other benefits as disclosed herein compared to using pure R-beta-hydroxybutyric acid.

Example 38

Any of the foregoing beta-hydroxybutyric acid compositions of Examples 17-36 can include a non-racemic mixture enriched with S-beta-hydroxybutyric acid, which can be prepared by mixing S-beta-hydroxybutyric acid with a racemic mixture of R- and S-beta-hydroxybutyric acids to provide greater than 50% and less than 100% by enantiomeric equivalents of S-beta-hydroxybutyric acid and less than 50% and greater than 0% by enantiomeric equivalents of R-beta-hydroxybutyric acid. Because the non-racemic mixture includes more of the S-enantiomer, the onset of ketosis is delayed for a given dosage as compared to the same dosage of a racemic mixture.

Example 39

Any of the foregoing beta-hydroxybutyric acid compositions of Examples 17-36 can include a racemic mixture of R-beta-hydroxybutyric acid and S-beta-hydroxybutyric acid to provide 50% by enantiomeric equivalents of the R-enantiomer and 50% by enantiomeric equivalents of the S-enantiomer. Because the composition contains a racemic mixture, the onset of ketosis is accelerated for a given dosage as compared to the same dosage enriched with the S-enantiomer. On the other hand, because the racemic mixture includes 50% by enantiomeric equivalents of the S-enantiomer, the duration of sustained ketosis is increased for a given dosage as compared to the same dosage enriched with the R-enantiomer.

Example 40

Any of the foregoing beta-hydroxybutyric acid compositions of Examples 17-39 is modified by including one or more supplements, such as one or more vitamins, minerals, herbs, and others known in the art.

Example 41

Any of the foregoing beta-hydroxybutyric acid compositions of Examples 17-40 is modified by including one or more beta-hydroxybutyrate esters.

Example 42

Any of the foregoing beta-hydroxybutyric acid compositions of Examples 17-41 is modified by including one or more fat burner supplements such as green tea, green tea extract (e.g., a composition including one or more isolated green tea catechins such as epigallocatechin gallate (EGCG)), green coffee extract, conjugated linoleic acid (CLA), tetradecyl thioacetic acid (TTA), *Coleus forskohlii* (i.e., forskolin), yohimbine, rauwolscine, capsaicin, raspberry ketones (e.g., 4-(4-hydroxyphenyl) butan-2-one, p-hydroxybenzyl acetone), ephedrine, synephrine (e.g., bitter orange extract), octopamine, 1,3-dimethylamylamine, higenamine, fucoxanthin, acetylcholine modulators and/or adenosine receptor antagonists (e.g., caffeine), nicotine, coca leaf derivative, ursolic acid, clenbuterol, noradrenaline reuptake inhibitors (e.g., hordenine, atomoxetine), 7-oxodehydroepiandrosterone (i.e., 7-keto DHEA), thyroid hormones (e.g., triiodothyronine), and combinations thereof. The resulting combined supplement is expected to provide greater lipolysis and/or fat oxidation effects than a similar dose that includes only beta-hydroxybutyrate compounds.

Example 43

Any of the foregoing beta-hydroxybutyric acid compositions of Examples 17-42 is modified by including one or more nootropic supplements such as tyrosine, L-DOPA (i.e., L-3,4-dihydroxyphenylalanine), tryptophan, and 5-hydroxytryptophan (5-HTP), racetams such as such as piracetam, oxiracetam, and aniracetam, L-theanine, D-serine, phosphatidylserine, tolcapone, uridine, vinpocetine, norepinephrine reuptake inhibitors such as hordenine and atomoxetine, *Panax ginseng, Ginkgo biloba, Rhodiola rosea, Polygala tenuifolia, Muira puama, Eschscholzia californica, Convolvulus pluricaulis, Centella asiatica, Evolvulus alsinoides, Bacopa monnieri*, Epimedium herbs, Ashwagandha herbs, cyclic adenosine monophosphate (cAMP) modulators such as forskolin, stimulants such as nicotine, caffeine, and amphetamines, cholinergic compounds and/or acetylcholine modulators such as huperzine-A, dimethylaminoethanol, choline, and alpha-glycerophosphocholine, and combinations thereof. The resulting combined supplement is expected to provide greater cognition, alertness, and/or mood effects than a similar dose that includes only beta-hydroxybutyrate compounds.

END OF EXAMPLES

In some implementations, one or more additives may be included in the composition, such as flavorings (e.g., natural and/or artificial), vitamins, minerals, binders, and/or any other appropriate additive. The additives may alter flavor, color, and/or texture. The additives may increase palatability and/or facilitate inclusion in a delivery vehicle (e.g., tablet, food product, beverage product such as a drink mix, etc.). The additive may be any appropriate solid and/or liquid to which the compound is added. For example, an additive may include liquid carriers, such as water, milk(s), and/or any other appropriate drinkable liquid. In some implementations, the composition may include a pharmaceutically inert liquid carrier, such as water (e.g., tap water, filtered water, distilled water, etc.). The liquid carrier may include other drinkable liquids such as coconut water, watermelon water, electrolyte water, and/or combinations thereof. The liquid carrier may include milks such as dairy milk, non-dairy milk, coconut milk, other milks, and/or combinations thereof. The liquid carrier may include an electrolyte solution, in some implementations.

The described compositions may be administered via any appropriate administration method. For example, the described compositions may be administered enterally and/or parenterally (referring to intravenous and intra-arterial and other appropriate parenteral routes). In some implementations, the described composition may be administered via a tablet and/or capsule. The described composition may be provided in a powdered form that allows the described composition to be sprinkled on food, mixed with a liquid to provide a beverage, and/or directly administered. The described composition may be provided in gel form. The compounds in the composition may be mixed, coupled to each other, and/or provided separately. For example, the composition may include beta-hydroxybutyrate coupled to another compound (e.g., beta-hydroxybutyrate ester and/or amino acid). In some implementations, the beta-hydroxybutyrate and one or more other compounds may be provided separately (e.g., in pills). An individual may sequentially and/or concurrently be administered (e.g., swallow pills) the beta-hydroxybutyrate and other compounds.

The described compositions may be administered on an administration protocol to cause weight loss and/or maintain a weight of an individual; elevate and/or maintain blood ketone levels; increase and/or maintain ketosis; and/or improve glucose tolerance (e.g., fasting glucose levels may be reduced and/or glucose metabolism may be improved), in some implementations. For example, the described compositions may be administered once a day, via an extended-release preparation, and/or multiple times a day (e.g., 1 to 5 times a day, 2 to 5 times a day, 3 to 5 times a day, etc.). The described composition may replace other pharmaceuticals or dietary supplements taken to promote weight loss, maintain a weight, promote ketosis, elevate blood ketone levels and/or be utilized in combination with one or more other pharmaceuticals or dietary supplements, as appropriate. The described composition may replace other pharmaceuticals or dietary supplements taken for improving glucose tolerance, such as metformin, and/or be utilized in combination with one or more other pharmaceuticals or dietary supplements, as appropriate, in some implementations.

In various implementations, the described composition(s) (e.g., butyrate, beta-hydroxybutyrate, R-beta-hydroxybutyrate, related compounds, and/or one or more other compounds) may include one or more of the described components, equivalent(s) of the described component(s), derivatives of the described component(s), complex(es) of the described component(s), salt(s) of the described component(s), and/or combinations thereof.

In various implementations, a pharmaceutically effective amount of one or more of the described composition(s) may be administered. Administration of the pharmaceutically effective amount may induce and/or maintaining ketosis; maintaining and/or promoting weight loss; increase mental processes (e.g., acuity including cognitive functioning, mood, energy, alertness, focus, performance, effects of aging, etc.); improve and/or maintain body composition; function as a therapeutic for one or more of the described conditions or disorders (e.g., treat neurological disorders); and/or combinations thereof.

Although various types of increases in mental acuity have been described, other features of mental acuity such as memory, focus, concentration, and/or understanding (e.g., speed of processing, accuracy of processing) may be increased by administration of an effective amount of the composition that includes R-beta-hydroxybutyrate.

Although a subject and/or an individual have been described as a human, a subject and/or individual may be a person or a group of people. Although various described systems and processes have been described as a being administered in humans, the described systems and processes may be administered to other mammals, such as rats, dogs, etc.

In various implementations, beta-hydroxybutyrate may administered simultaneously and/or sequentially with one or more other compounds (e.g., short chain, medium chain, and/or long chain fatty acids). For example, beta-hydroxybutyrate and/or one or more other compounds may be delivered mixed in a powdered, liquid, gel, and/or other appropriate form. In some implementations, the beta-hydroxybutyrate and/or one or more other compounds may be administered via pills, tablets, capsules, other oral administration forms, parenterally, intravenously, nasal sprays, sublingual tabs/strips, or topical delivery, rectal, other appropriate administration forms, and/or combinations thereof.

Although the term beta-hydroxybutyrate is the terminology used in the described implementations, beta-hydroxybutyrate is also referred to as beta-hydroxybutyrate, (R)-3-Hydroxybutyric acid, (R)-3-Hydroxybutanoic acid, (3R)-3-hydroxybutanoic acid, (R)-3-Hydroxybutanoate, (R)-(−)-3-Hydroxybutyric acid, (R)-(−)-beta-hydroxybutyric acid, 3-D-hydroxybutyrate, BHIB, BHB, 3-delta-hydroxybutyrate, delta-3-hydroxybutyrate, 3-D-hydroxybutyric acid, D-3-hydroxybutyric acid, 3R-hydroxybutanoic acid, delta-beta-hydroxybutyrate, D-3-hydroxybutyrate, D-(−)-3-hydroxybutyrate, delta-3-hydroxybutyric acid, (−)-3-Hydroxybutyric acid, D-beta-hydroxybutyrate, (R)-(−)-b-Hydroxybutyrate, (R)-beta-Hydroxybutyric acid, delta-(−)-3-hydroxybutyrate, (R)-3-hydroxybutyrate, (R)-beta-hydroxybutanoic acid, (R)-(−)-beta-hydroxybutyrate, (−)-3-Hydroxy-n-butyric acid, (R)-(−)-β-hydroxybutyric acid, butanoic acid, 3-hydroxy-, (R)-butyric acid, 3-hydroxy-, D-(−)-(R)-3-82578-46-9, beta-D-hydroxybutyric acid, D-beta-hydroxybutyric acid, (3R)-3-delta-hydroxybutyric acid, 3-(R)-hydroxybutyric acid, and/or (−)-beta-hydroxybutyrate.

In various implementations, beta-hydroxybutyrate is described as included in a composition; administered in an amount, form, and/or schedule; and/or being in a particular form (e.g., complexed and/or coupled). R-beta-hydroxybutyrate may be utilized in the various described implementations of beta-hydroxy butyrate in the same or lower amount as the described beta-hydroxybutyrate, as appropriate.

It is to be understood the implementations are not limited to particular systems or processes described which may, of course, vary. It is also to be understood that the terminology used herein is for the purpose of describing particular implementations only and is not intended to be limiting. As used in this specification, the singular forms "a", "an" and "the" include plural referents unless the content clearly indicates otherwise. Thus, for example, reference to "a compound" includes a combination of two or more compounds and reference to "a beta-hydroxybutyrate" includes different types and/or combinations of beta-hydroxybutyrate.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A composition for administering ketone bodies to a subject, comprising:

a non-racemic mixture of R-beta-hydroxybutyrate and S-beta-hydroxybutyrate enriched with R-beta-hydroxybutyrate so as to contain more than 50% and less than 100% by enantiomeric equivalents of R-beta-hydroxybutyrate and less than 50% and more than 0% by enantiomeric equivalents of S-beta-hydroxybutyrate.

2. The composition of claim 1, wherein the non-racemic mixture contains from 50.5% to 99.5% by enantiomeric equivalents of R-beta-hydroxybutyrate and 49.5% to 0.5% by enantiomeric equivalents of S-beta-hydroxybutyrate.

3. The composition of claim 1, wherein the non-racemic mixture contains from 51% to 99% by enantiomeric equivalents of R-beta-hydroxybutyrate and 49% to 1% by enantiomeric equivalents of S-beta-hydroxybutyrate.

4. The composition of claim 1, wherein the non-racemic mixture contains from 52% to 98% by enantiomeric equivalents of R-beta-hydroxybutyrate and 48% to 2% by enantiomeric equivalents of S-beta-hydroxybutyrate.

5. The composition of claim 1, wherein the non-racemic mixture contains from 53% to 97% by enantiomeric equivalents of R-beta-hydroxybutyrate and 47% to 3% by enantiomeric equivalents of S-beta-hydroxybutyrate.

6. The composition of claim 1, wherein the non-racemic mixture contains from 55% to 96% by enantiomeric equivalents of R-beta-hydroxybutyrate and 45% to 4% by enantiomeric equivalents of S-beta-hydroxybutyrate.

7. The composition of claim 1, wherein the non-racemic mixture contains from 57% to 93% by enantiomeric equivalents of R-beta-hydroxybutyrate and 43% to 7% by enantiomeric equivalents of S-beta-hydroxybutyrate.

8. The composition of claim 1, wherein the non-racemic mixture contains from 60% to 90% by enantiomeric equivalents of R-beta-hydroxybutyrate and 40% to 10% by enantiomeric equivalents of S-beta-hydroxybutyrate.

9. The composition of claim 1, wherein the non-racemic mixture contains from 65% to 85% by enantiomeric equivalents of R-beta-hydroxybutyrate and 35% to 15% by enantiomeric equivalents of S-beta-hydroxybutyrate.

10. The composition of claim 1, wherein the non-racemic mixture comprises one or more R-beta-hydroxybutyrate salts and one or more S-beta-hydroxybutyrate salts.

11. The composition of claim 1, wherein the non-racemic mixture comprises one or more R-beta-hydroxybutyrate esters and one or more S-beta-hydroxybutyrate esters.

12. The composition of claim 1, wherein the non-racemic mixture comprises R-beta-hydroxybutyric acid and S-beta-hydroxybutyric acid.

13. The composition of claim 1, wherein the non-racemic mixture of R-beta-hydroxybutyrate and S-beta-hydroxybutyrate is a mixed salt-acid composition that includes at least one R-beta-hydroxybutyrate salt, at least one S-beta-hydroxybutyrate salt, and at least one of R-beta-hydroxybutyric acid or S-beta-hydroxybutyric acid.

14. The composition of claim 13, wherein the mixed salt-acid composition comprises 75% to 99.9% by molar equivalents of combined R-beta-hydroxybutyrate and S-beta-hydroxybutyrate salts and 0.1% to 25% by molar equivalents of combined R-beta-hydroxybutyric acid and S-beta-hydroxybutyric acid.

15. The composition of claim 1, further comprising 1,3-butanediol.

16. The composition of claim 1, further comprising at least one medium chain fatty acid having from 6 to 12 carbons, or a mono-, di- or triglyceride of the at least one medium chain fatty acid.

17. A composition for administering ketone bodies to a subject, comprising:

a non-racemic mixture of R-beta-hydroxybutyrate and S-beta-hydroxybutyrate enriched with R-beta-hydroxybutyrate so as to contain more than 50% and less than 100% by enantiomeric equivalents of R-beta-hydroxybutyrate and less than 50% and more than 0% by enantiomeric equivalents of S-beta-hydroxybutyrate, wherein the composition is provided as or in a tablet, capsule, powder, food product, food additive, flavored beverage, vitamin fortified beverage, non-alcoholic beverage, flavored beverage additive, vitamin fortified beverage additive, non-alcoholic beverage additive, candy, sucker, pastille, food supplement, flavored mouth spray, or suppository.

18. The composition of claim 17, wherein the non-racemic mixture contains from 50.5% to 99.5% by enantiomeric equivalents of R-beta-hydroxybutyrate and 49.5% to 0.5% by enantiomeric equivalents of S-beta-hydroxybutyrate.

19. A composition for administering ketone bodies to a subject, comprising:

a dietetically or pharmaceutically acceptable carrier selected from the group consisting of tablet, capsule, powder, food product, food additive, flavored beverage, vitamin fortified beverage, non-alcoholic beverage, flavored beverage additive, vitamin fortified beverage additive, non-alcoholic beverage additive, candy, sucker, pastille, food supplement, flavored mouth spray, and suppository; and a non-racemic mixture of R-beta-hydroxybutyrate and S-beta-hydroxybutyrate enriched with R-beta-hydroxybutyrate so as to contain more than 50% and less than 100% by enantiomeric equivalents of R-beta-hydroxybutyrate and less than 50% and more than 0% by enantiomeric equivalents of S-beta-hydroxybutyrate.

20. The composition of claim 19, wherein the non-racemic mixture contains from 50.5% to 99.5% by enantiomeric equivalents of R-beta-hydroxybutyrate and 49.5% to 0.5% by enantiomeric equivalents of S-beta-hydroxybutyrate.

* * * * *